(12) United States Patent
Hegde et al.

(10) Patent No.: US 6,949,576 B2
(45) Date of Patent: *Sep. 27, 2005

(54) INSECTICIDAL 3-(2,6-DISUBSTITUTED PHENYL)-5-[5-ARYLTHIEN-3-YL]-1,2,4-TRIAZOLES

(75) Inventors: Vidyadhar Babu Hegde, Carmel, IN (US); Scott Jerome Bis, Midland, MI (US); Maurice Chee Hoong Yap, Zionsville, IN (US); Denise Marie Perreault, Indianapolis, IN (US); Francis Eugene Tisdell, Carmel, IN (US); Leonard Paul Dintenfass, Indianapolis, IN (US); James Edwin Dripps, Carmel, IN (US); James Michael Gifford, Lebanon, IN (US); Katherine Anne Guenthenspberger, Daleville, IN (US); Laura Lee Karr, Lebanon, IN (US); Joe Raymond Schoonover, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/664,145

(22) Filed: Sep. 17, 2003

(65) Prior Publication Data

US 2004/0072887 A1 Apr. 15, 2004

Related U.S. Application Data

(62) Division of application No. 10/244,124, filed on Sep. 13, 2002, now Pat. No. 6,770,665.
(60) Provisional application No. 60/322,236, filed on Sep. 14, 2001.

(51) Int. Cl.$^7$ .................. A61K 31/41; C07P 249/08
(52) U.S. Cl. .................. 514/383; 548/266.2
(58) Field of Search .................. 514/383; 548/266.2

(56) References Cited

U.S. PATENT DOCUMENTS

| | | | |
|---|---|---|---|
| 5,482,951 A | 1/1996 | Ozaki et al. | 514/340 |
| 6,015,826 A | 1/2000 | Pechacek et al. | 514/383 |
| 6,262,305 B1 * | 7/2001 | Pechacek et al. | 564/248 |
| 6,770,665 B2 * | 8/2004 | Hegde et al. | 514/383 |

FOREIGN PATENT DOCUMENTS

| | | |
|---|---|---|
| EP | 572142 | 7/1996 |
| JP | 8-192224 | 4/1996 |
| JP | 8-283261 | 10/1996 |

* cited by examiner

*Primary Examiner*—Kamal A Saeed
*Assistant Examiner*—Robert Shiao
(74) *Attorney, Agent, or Firm*—Craig Nixon

(57) ABSTRACT

Triazole compounds having a 2,6-disubstituted-phenyl group in the 3-position, 5'-arylthien-3-yl group in the 5-position and an alkyl group in the 1-position are effective in controlling lepidoptera, coleoptera, mites and other sucking pests.

21 Claims, No Drawings

INSECTICIDAL 3-(2,6-DISUBSTITUTED PHENYL)-5-[5-ARYLTHIEN-3-YL]-1,2,4-TRIAZOLES

This application is a division of application Ser. No. 10/244,124 filed on Sep. 13, 2002 now U.S. Pat. No. 6,770,665. This application claims the benefit of U.S. Provisional Application No. 60/322,236, filed Sep. 14, 2001.

BACKGROUND OF THE INVENTION

The present invention concerns novel 3-(2,6-disubstituted phenyl)-5-(4- or 5-arylthien-2- or -3-yl)-1,2,4-triazoles and their use in controlling lepidoptera, coleoptera, mites and other sucking pests. This invention also includes new synthetic procedures, intermediates for preparing the compounds, pesticide compositions containing the compounds, and methods of controlling lepidoptera, coleoptera, mites and sucking pests using the compounds.

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or a typical modes of action.

A number of 3,5-diphenyl-1H-1,2,4-triazole derivatives have been described in the literature as having acaricidal activity (U.S. Pat. No. 5,482,951; JP 8092224, EP 572142, JP 08283261). U.S. Pat. No. 6,015,826 discloses certain 3-(substituted phenyl)-5-(thienyl)-1,2,4-triazoles and their use in controlling certain insects and mites, viz., aphids, mites and whiteflies. The present invention provides novel compounds with broad-spectrum activity against lepidoptera and coleoptera in addition to mites and other sucking pests.

SUMMARY OF THE INVENTION

This invention concerns compounds especially useful for the control of lepidoptera, coleoptera, mites and other sucking pests. More specifically, the invention concerns compounds of the formula (1)

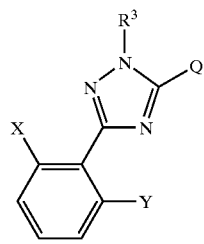

(1)

wherein

Q represents

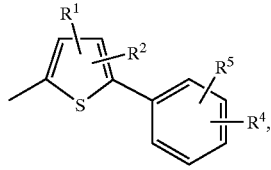

$Q^1$

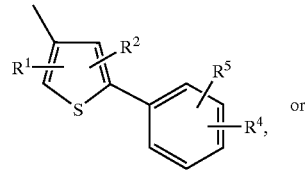

$Q^2$ or

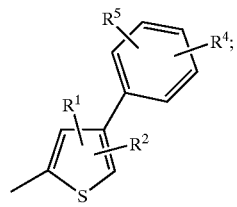

$Q^3$

X and Y independently represent Cl or F;
$R^1$ and $R^2$ independently represent H, $C_1$–$C_6$ alkyl or halogen, provided that when Q is $Q^1$ or $Q^3$, then $R^1$ and $R^2$ are not both H;
$R^3$ represents $C_1$–$C_3$ alkyl;
$R^4$ represents halogen, $C_1$–$C_6$ alkyl, $C_1$–$C_6$ alkoxy, $C_1$–$C_6$ thioalkyl, $C_3$–$C_6$ alkoxyalkoxy, $C_1$–$C_6$ haloalkyl, $C_1$–$C_6$ haloalkoxy, $C_1$–$C_6$ halothioalkyl, $C_3$–$C_6$ alkenyloxy, or phenoxy;
$R^5$ represents H, halogen or a $C_1$–$C_6$ alkyl ether or haloalkyl ether, which, when taken together with $R^4$, forms a 5- or 6-membered ring containing 1 or 2 oxygen atoms;
or a phytologically acceptable acid addition salt thereof.

Preferred compounds of formula (1) include the following classes:

(1) Compounds of formula (1) wherein X and Y are both F.
(2) Compounds of formula (1) wherein X and Y are both Cl.
(3) Compounds of formula (1) wherein X is F and Y is Cl (more preferred).
(4) Compounds of formula (1) wherein Q is $Q^1$ or $Q^3$.
(5) Compounds of formula (1) wherein Q is $Q^2$.
(6) Compounds of formula (1) wherein $R^1$ is $CH_3$, $CH_2CH_3$ or Cl when Q is $Q^1$ or $Q^3$, more preferably $R^1$ is $CH_3$.
(7) Compounds of formula (1) wherein $R^1$ is H, $CH_3$, $CH_2CH_3$, Cl or Br when Q is $Q^2$, more preferably $R^1$ is H or $CH_3$.
(8) Compounds of formula (1) wherein $R^2$ is H, $CH_3$, $CH_2CH_3$, Cl or Br, more preferably $R^2$ is H or $CH_3$.
(9) Compounds of formula (1) wherein $R^4$ is F, Cl, $CF_3$, haloalkoxy or phenoxy, more preferably $R^4$ is haloalkoxy.
(10) Compounds of formula (1) wherein $R^4$ is in the 4-position of the phenyl ring.
(11) Compounds of formula (1) wherein $R^5$ is H, F, Cl, or $CF_3$.
(12) Compounds of formula (1) wherein $R^3$ is $CH_3$.

It will be appreciated by those skilled in the art that the most preferred compounds are generally those which are comprised of combinations of the above preferred classes.

The invention also provides new processes and intermediates for preparing compounds of formula (1) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the terms "alkyl" and "alkenyl", as well as derivative terms such as "alkoxy", "alkenyloxy" and "thioalkyl", as used herein, include within their scope straight chain, branched chain and cyclic moieties. The term "alkenyl" is intended to include one or more unsaturated bonds.

Unless specifically limited otherwise, the term "halogen", as well as derivative terms such as "halo", as used herein, refers to fluorine, chlorine, bromine, and iodine. Preferred halogens are fluorine and chlorine.

The terms "haloalkyl" and "haloalkenyl" refer to alkyl and alkenyl groups substituted with from one up to the maximum possible number of halogen atoms. The terms "haloalkoxy" and "halothioalkyl" refer to alkoxy and thioalkyl groups substituted with from one up to the maximum possible number of halogen atoms.

The term "alkoxyalkoxy" refers to an alkoxy group substituted with an alkoxy group. The term "alkyl ether" refers to an alkylene oxide group which can be bonded either through the carbon or the oxygen atom.

Unless otherwise indicated, when it is stated that a group may be substituted with one or more substituents selected from an identified class, it is intended that the substituents may be independently selected from the class.

Synthesis

Compounds of formula (1) can be prepared by the methods illustrated in Scheme A:

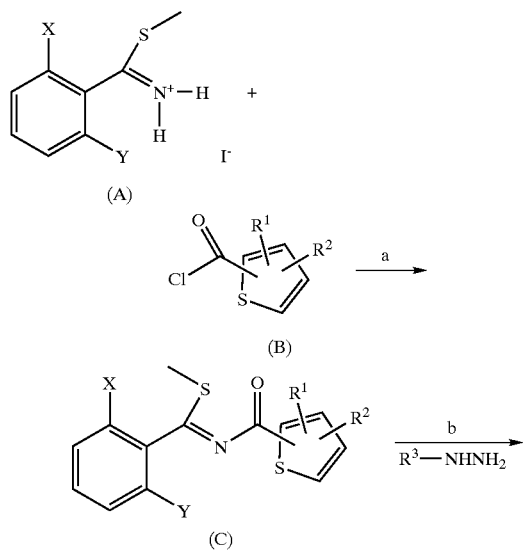

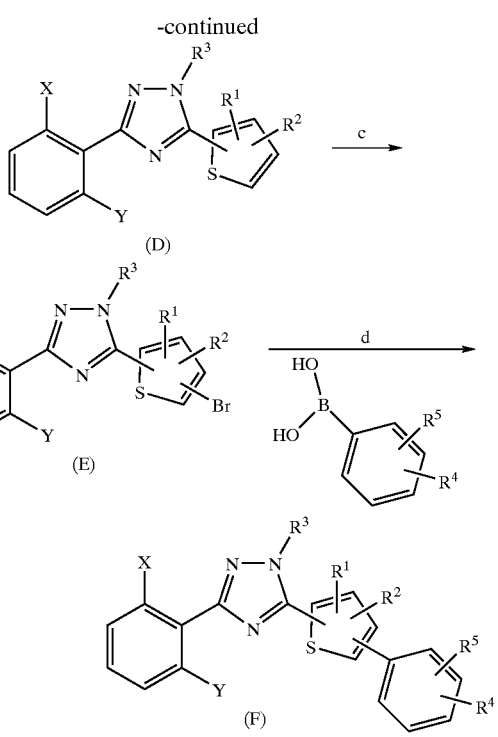

wherein X, Y, $R^1$, $R^2$, $R^3$, $R^4$ and $R^5$ are defined as in formula (1).

In step a of Scheme A, the compound of formula (A) is coupled with the acid chloride of formula (B) to provide acyl thioimidate of formula (C). Pyridine is the preferred base for coupling, however any organic or inorganic base can be used. Acid chlorides of formula (B) are prepared from corresponding carboxylic acids of formula (G)

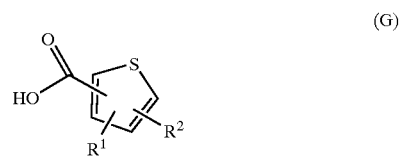

which are either commercially available or are readily made through known procedures.

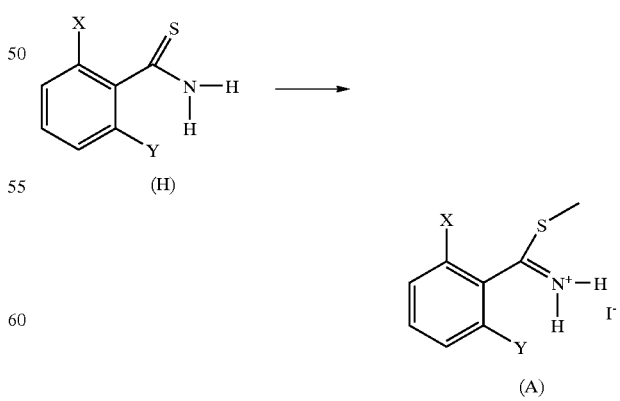

Thioimidates (A) are readily available through alkylation of the corresponding thioamides (H) which themselves are commercially available or can be made from the amide (*Phosphorus Sulfur*, 1985, 25, 297–305) or nitrile (*Chem.-Ztg.* 1980, 104, 365; *J. Chem. Soc.* 1952, 742; *Can. J. Chem.* 1985, 63, 3075).

In the cyclization step b of Scheme A, the compound of formula (C) can be reacted with hydrazine or a substituted hydrazine in toluene at 25 to 110° C. to afford the triazole intermediate (D) in good yield with a high degree of regiospecificity. Instead of toluene other aprotic solvents such as tetrahydrofuran (THF) can also be used.

In step c of Scheme A, the compound of formula (D) can be brominated with bromine in acetic acid in the presence or absence of sodium acetate at 25° C. to refluxing temperature to afford the compound of formula (E).

In the Suzuki coupling step d of Scheme A, the compound of formula (E) can be reacted with an appropriately substituted $R^4/R^5$—boronic acid to provide the compound of formula (F). The coupling can be carried out in an acetonitrile/water mixture or ethanol, at a temperature in the range from ambient to refluxing. Catalytic amounts of dichlorobis(triphenylphosphine)palladium(II) or tetrakis (triphenylphosphine)palladium(0) are typically used for coupling, however other Pd(II) or Pd(0) catalysts can also be used. Typically sodium carbonate is used as a base in the reaction, however other inorganic bases such as potassium carbonate or organic bases such as triethylamine can also be used.

Alternatively, compounds of formula (1) can also be prepared by the methods illustrated in Scheme B:

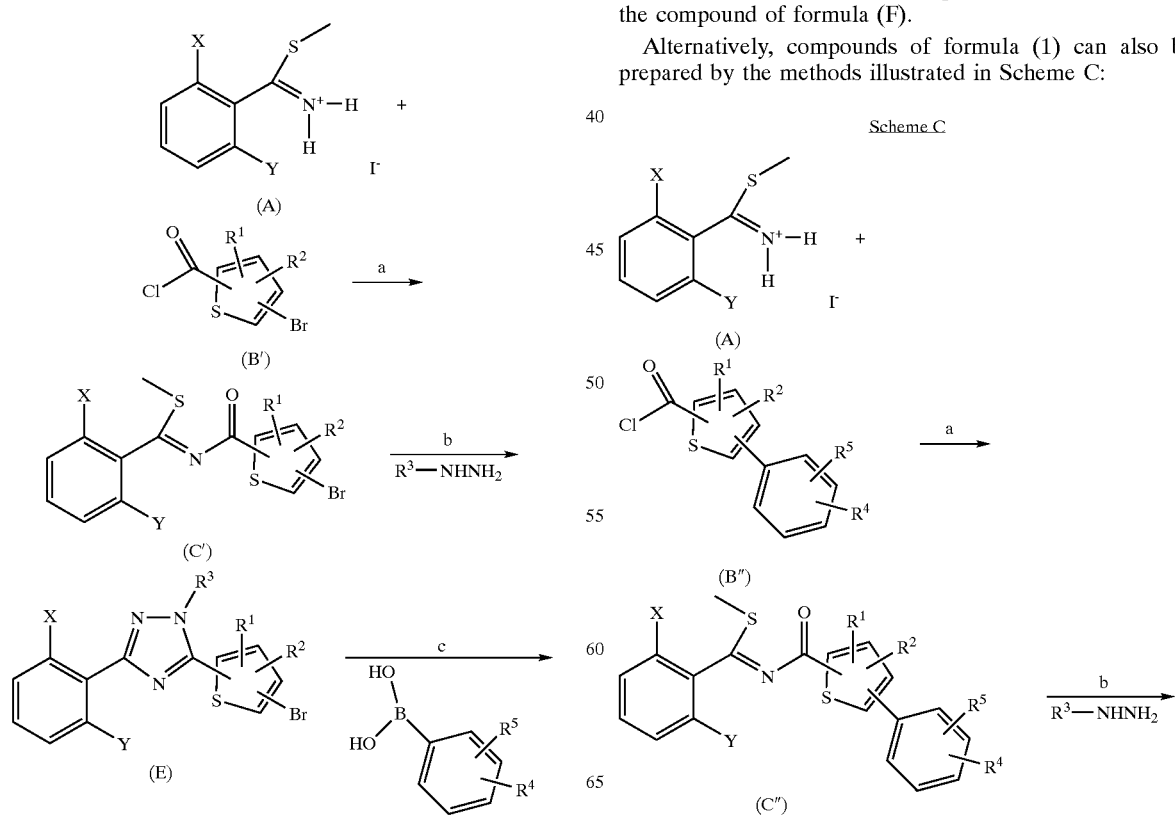

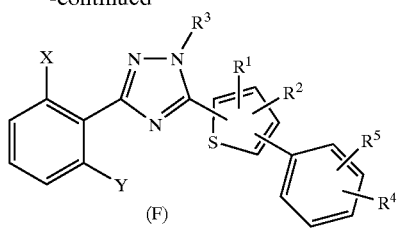

wherein X, Y, R, $R^2$, $R^3$, $R^4$ and $R^5$ are defined as in formula (1).

In step a of Scheme B, the compound of formula (A) is coupled with the acid chloride of formula (B') to provide acyl thioimidate of formula (C') in a similar fashion as described for step a in Scheme A. Acid chlorides of formula (B') are prepared from corresponding carboxylic acids of formula (G')

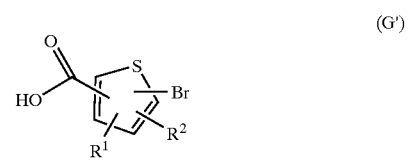

which are readily made through known procedures.

The cyclization step b of Scheme B is performed in a similar fashion as step b of Scheme A to afford the triazole intermediate (E) in good yield with a high degree of regioselectivity.

In step c of Scheme B, the Suzuki coupling was performed in a similar fashion as step d of Scheme A to afford the compound of formula (F).

Alternatively, compounds of formula (1) can also be prepared by the methods illustrated in Scheme C:

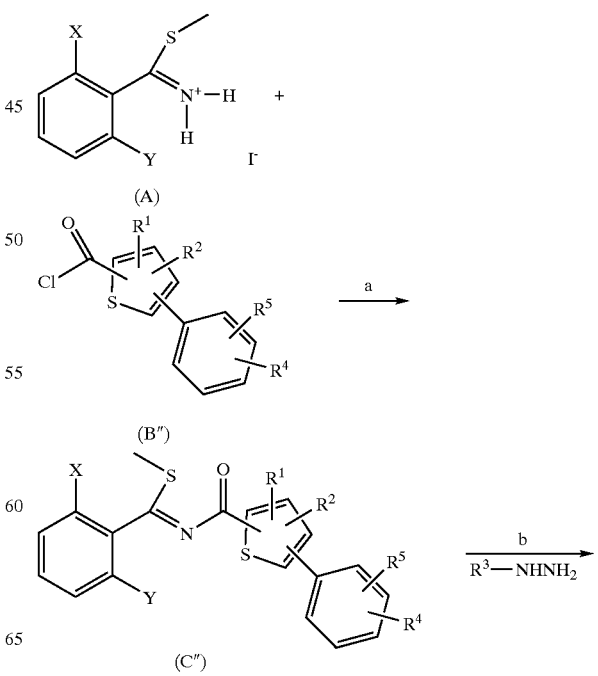

-continued

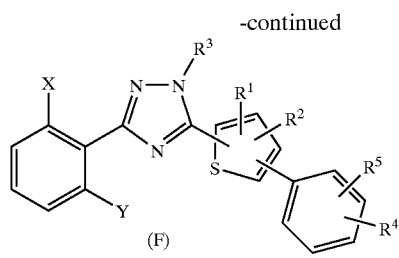

wherein X, Y, R¹, R², R³, R⁴ and R⁵ are defined as in formula (1).

In step a of Scheme C, the compound of formula (A) is coupled with the acid chloride of formula (B") to provide acyl thioimidate of formula (C") in a similar fashion as described for step a in Scheme A. Acid chlorides of formula (B") are prepared from corresponding carboxylic acids of formula (G")

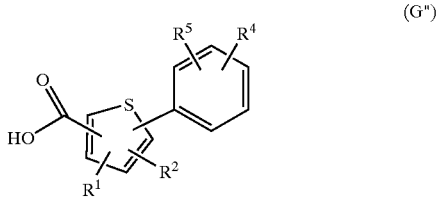

which are readily made through known procedures.

The cyclization step b of Scheme C is performed in a similar fashion as step b of Scheme B to afford the triazole (F).

EXAMPLES

Example A 2,4-Dimethylthiophene-3-carboxylic acid

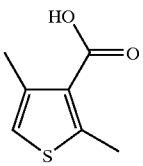

n-Butyllithium (2.5 M in hexanes, 18.6 mL, 46 mmol) was added to a pre-cooled solution of 4-methylthiophene-3-carboxylic acid (3.0 g, 21 mmol) in dry tetrahydrofuran (THF, 35 mL) at −62° C. The reaction mixture was stirred at −78° C. for an hour, allowed to warm to −40° C. and re-cooled to −78° C. before adding iodomethane (3.28 mL, 7.49 g, 53 mmol). After addition, the reactants were stirred at −78° C. for an hour and then allowed to warm to room temperature over 14 hours and quenched with water (20 mL). The organic phase was extracted with dilute sodium hydroxide (0.2 N, 3×30 mL). The combined aqueous extracts were washed with ether (2×30 mL), cooled in an ice bath and acidified to pH 3 using concentrated hydrochloric acid. The resultant precipitate was extracted with ether (3×50 mL). The combined ethereal extracts were washed with water (50 mL) and brine (50 mL), dried over magnesium sulphate, concentrated under reduced pressure and recrystallised from ethyl acetate/hexane to give product as an amorphous white solid (2.7 g, 82%): mp 164–165° C.; ¹H NMR (CDCl₃) δ 6.65 (q, 1H), 2.73 (s, 3H), 2.43 (d, 3H); EI/MS 156 m/e (M⁺); IR (liq film) 1664 cm⁻¹; Calcd for C₇H₈O₂S: C, 53.8; H, 5.16; Found: C, 53.8; H, 5.11.

Example B

5-Bromo-2,4-dimethylthiophene-3-carboxylic acid

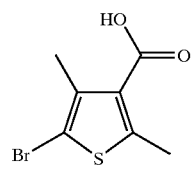

A solution of bromine (0.73 mL, 2.25 g, 14 mmol) in glacial acetic acid (8 mL) was added to a solution of 2,4-dimethylthiophene-3-carboxylic acid (2.1 g, 13 mmol) in glacial acetic acid (24 mL) at 6° C. Upon completion, the reaction was stirred at 10° C. for an hour, diluted with glacial acetic acid (30 mL), stirred for 14 hours at room temperature, poured into water (400 mL) and extracted with ether (3×40 mL). The combined ethereal extracts were extracted with dilute sodium hydroxide (0.2 N, 3×30 mL). The combined basic extracts were cooled in an ice bath and then acidified to pH 3 using concentrated hydrochloric acid. Precipitated solids were extracted with ether (3×40 mL). Pooled organic extracts were washed with water (50 mL) and brine (50 mL), dried over magnesium sulphate and concentrated under reduced pressure. The residue was recrystallised from ethyl acetate/hexane to give product as an amorphous white solid (2.7 g, 85%): mp 183–184° C.; ¹H NMR (CDCl₃) δ 2.67 (s, 3H), 2.38 (s, 3H); EI/MS 235 m/e (M⁺); IR (liq film) 1674 cm⁻¹; Calcd. for C₇H₇BrO₂S: C, 35.8; H, 3.00; S, 13.6; Found: C, 35.8; H, 2.99; N, 13.5.

Example C

Ethyl 4,5-dibromo-3-chlorothiophene-2-carboxylate

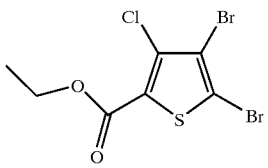

Ethyl 3-chlorothiophene-2-carboxylate (3.96 g, 20.7 mol) in a suspension of sodium acetate (12.71 g, 154 mmol) and glacial acetic acid (35 mL) was treated with bromine (9.6 mL, 186.3 mmol). The reaction mixture was stirred at 75° C. under N₂ for 136 hours and then at 25° C. for 144 hours. The reaction mixture was poured onto ice cold satd aq sodium bicarbonate and aq sodium metabisulfite. The mixture was stirred with ether (100 mL) for 30 minutes. Extraction with ether (3×150 mL) gave an organic layer that was washed with water (150 mL) and satd aq sodium chloride (150 mL), dried over magnesium sulfate and concentrated to give product as a white solid (5.83 g, 80%): mp 58–63° C.; ¹H NMR (CDCl₃) δ 4.37 (q, 2H, J=7.1 Hz), 1.38 (t, 3H, J=7.1 Hz,); EI/MS 347 m/e (M⁺).

Example D 4,5-Dibromo-3-chlorothiophene-2-carboxylic acid

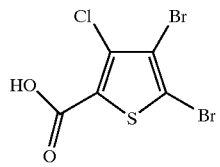

Ethyl 4,5-dibromo-3-chlorothiophene-2-carboxylate (5.52 g, 15.8 mmol) and lithium hydroxide (0.716 g, 31.7 mmol) were taken up in mixture of THF (30 mL) and water (30 mL). The reaction mixture was stirred at 25° C. for 32 hours. The aqueous layer was made acidic by the dropwise addition of conc hydrochloric acid and extracted with ether (3×50 mL). The combined organic extracts were dried over sodium sulfate, filtered and concentrated to give the product as a white solid (4.38 g, 86%) that was used without purification: mp 209–223° C. (d); $^1$H NMR (CDCl$_3$ and DMSO-d$_6$) δ 4.15 (bs, 1H); EI/MS 320 m/e (M$^+$).

Example E

Methyl 2-chloro-6-fluoro-N-[(4-methylthien-3-yl)carbonyl]benzenecarbimido-thioate

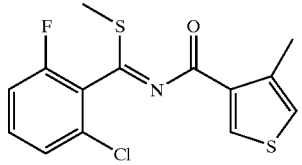

To a suspension of 4-methylthiophene-3-carboxylic acid (2.74 g, 19 mmol) in 1,2-dichloroethane (DCE, 100 mL) was added thionyl chloride (5.67 mL, 9.25 g, 78 mmol) and dimethylformamide (DMF, 10 drops from a Pasteur pipette). After refluxing under nitrogen for 4 hours, the reaction mixture was concentrated under reduced pressure. The residue was taken up in DCE (80 mL) and concentrated once again under reduced pressure. This residue was dissolved in DCE (30 mL) and added at a dropwise rate into a suspension of S-methylthio-2-chloro-6-fluorobenzamidinium bromide (5.5 g, 19 mmol) in DCE (50 mL) at −3° C. Upon completion, a solution of dry pyridine (4.72 mL, 4.61 g, 58 mmol) in DCE (3 mL) was added at a rate required to maintain the temperature below 0° C. The reaction was allowed to come to room temperature over 14 hours, washed with water (100 mL), saturated aqueous sodium carbonate (100 mL) and brine (70 mL), dried over magnesium sulphate and concentrated under reduced pressure to leave a thick, yellow liquid which solidified upon standing at room temperature for several hours (4.33 g, 68%): $^1$H NMR (CDCl$_3$) δ 8.09 (d, 1H), 7.27–7.32 (m, 1H), 7.16 (d, 1H), 7.00 (t, 1H), 6.87 (d, 1H), 2.58 (s, 3H), 2.34 (s, 3H); EI/MS: 327 m/e (M-1); IR (liq film) 1669, 1612 and 1599 cm$^{-1}$.

The following compounds were prepared according to the general procedure of Example E.

Methyl 2-chloro-N-[(4,5-dibromo-3-chlorothien-2-yl)carbonyl]-6-fluorobenzene-carbimidothioate

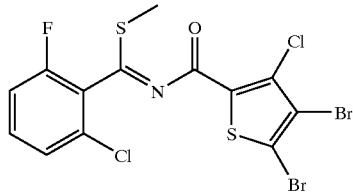

Product was isolated as a burnt orange solid (73% yield): mp 111–118° C.; $^1$H NMR (CDCl$_3$) δ 7.32 (ddd, 1H, J=5.8, 8.0, 8.4 Hz), 7.19 (d, 1H, J=8.0 Hz), 7.03 (ddd, 1H, J=0.85, 8.0, 8.4 Hz) 2.65 (s, 3H); EI/MS 470 m/e (M-Cl).

Methyl 2-chloro-N-[(4-chlorothien-3-yl)carbonyl]-6-fluorobenzenecarbimidothioate

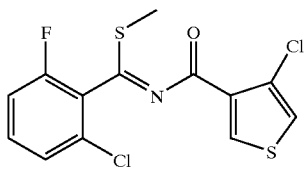

Product was isolated as a dark brown liquid that turned to a waxy solid over time (85% yield): $^1$H NMR (CDCl$_3$) δ 8.12 (d, 1H, J=3.6 Hz), 7.33–7.25 (m, 2H), 7.18 (dd, 1H, J=1.09, 0.73 Hz), 7.14 (d, 1H, J=3.6 Hz), 7.03 (dd, 1H, J=1.09, 8.4 Hz), 2.60 (s, 3H); EI/MS 348 m/e (M$^+$).

Example F 3-(2-Chloro-6-fluorophenyl)-1-methyl-5-(4-methylthien-3-yl)-1H-1,2,4-triazole

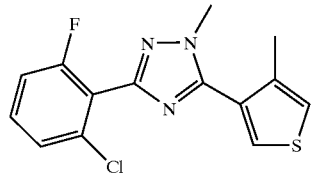

A solution of methylhydrazine (2.02 mL, 1.75 g, 38 mmol) in toluene (5 mL) was added at a rapid dropwise rate to a solution of methyl 2-chloro-6-fluoro-N-[(4-methylthien-3-yl) carbonyl]benzenecarbimidothioate (4.15 g, 12.7 mmol) in dry toluene (100 mL) at 55° C. The reaction was stirred at this temperature for 10 minutes and then left at room temperature for 14 hours. Another identical portion of methylhydrazine in toluene was added at room temperature and the reaction was heated at 80° C. for 3 hours and refluxed for an additional 3 hours. After cooling to room temperature, the reaction mixture was washed with water (100 mL), dilute hydrochloric acid (0.05 N, 2×100 mL) and brine (70 mL), dried over magnesium sulphate and concentrated under reduced pressure. The residue was recrystallised from ethyl acetate/hexane to give white cubes. The mother liquor was chromatographed (eluant, 30:9:1 hexane/ methylene chloride/acetonitrile to afford the product (3.25 g, 84%): mp 153–155° C.; ¹H NMR (CDCl₃) δ 7.54 (d, 1H), 7.26–7.38 (m, 2H), 7.06–7.13 (m, 2H), 3.98 (s, 3H), 2.35 (d, 3H); ¹⁹F NMR (external reference) −110 ppm; EI/MS 307 m/e (M−1).

The following compounds were prepared according to the general procedure of Example F.

3-(2-Chloro-6-fluorophenyl)-5-(4,5-dibromo-3-chlorothien-2-yl)-1-methyl-1H-1,2,4-triazole

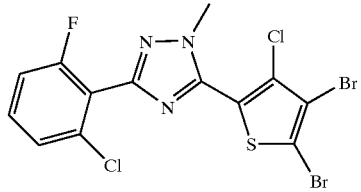

Product was isolated as a tan solid (24% yield): mp 180–182° C.; ¹H NMR (CDCl₃) δ 7.40–7.27 (m, 2H), 7.14–7.08 (m, 1H), 4.03 (s, 3H); EI/MS 485 m/e (M⁺).

3-(2-Chloro-6-fluorophenyl)-5-(4-chlorothien-3-yl)-1-methyl-1H-1,2,4-triazole

Product was isolated as a tan solid (28% yield): mp 126–133° C.; ¹H NMR (CDCl₃) δ 7.72 (d, 1H, J=3.6 Hz), 7.39–7.28 (m, 3H), 7.13–7.07 (m, 1H), 3.96 (s, 3H); EI/MS 327 m/e (M⁺); Calcd for C₁₃H₈Cl₂FN₃S: C, 47.58; H, 2.46; N, 12.80; S, 9.77; Found: C, 47.45; H, 2.40; N, 12.56; S, 9.51.

Example G 3-(2-Chloro-6-fluorophenyl)-(5-bromo-4-methylthien-3-yl)-1-methyl-1H-1,2,4-triazole

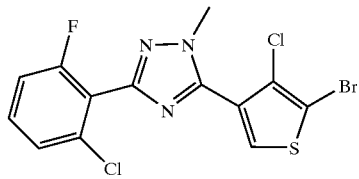

A suspension of 3-(2-chloro-6-fluorophenyl)-1-methyl-5-(4-methylthien-3-yl)-1H-1,2,4-triazole (2.35 g, 7.6 mmol) in glacial acetic acid (15 mL) was heated to 45° C. in order to effect solubilization. After cooling to 10° C., a solution of bromine (1.34 g, 0.43 mL, 8.4 mmol) in glacial acetic acid (4 mL) was added and the thick gel formed was stirred for 14 hours at room temperature. The reaction mixture was poured into cold water (100 mL) and extracted with ether (3×70 mL). The combined ethereal extracts were washed with water (100 mL), saturated aqueous sodium bicarbonate (2×100 mL), aqueous sodium bisulphite (10% solution, 300 mL) and brine (100 mL), dried over magnesium sulphate and concentrated under reduced pressure. Recrystallisation from ethyl acetate/hexane afforded yellow cubes. The mother liquor was chromatographed over silica gel to afford the product as colorless cubes (2.6 g, 89%): mp 133–134° C.; ¹H NMR (CDCl₃) δ 7.51 (s, 1H), 7.29–7.39 (m, 2H), 7.11 (t, 1H), 3.98 (s, 3H), 2.27 (s, 3H); EI/MS 386 m/e (M⁺).

The following compounds were prepared according to the general procedure of Example G.

3-(2,6-Difluorophenyl)-5-(5-bromo-3-chlorothien-2-yl)-1-methyl-1H-1,2,4-triazole

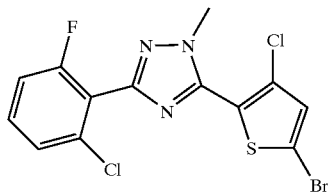

Product was isolated as a white solid (51% yield): mp 134–137° C.; ¹H NMR (CDCl₃) δ 7.43–7.33 (m, 1H), 7.08 (s, 1H), 7.06–6.98 (m, 2H), 4.02 (s, 3H); EI/MS 391 m/e (M+H); Calcd for C₁₃H₇BrClF₂N₃S: C, 39.97; H, 1.81; N, 10.76; S, 8.21; Found: C, 39.74; H, 1.82; N, 10.54; S, 8.27.

3-(2-Chloro-6-fluorophenyl)-5-(5-bromo-4-chlorothien-3-yl-1-methyl-1H-1,2,4-triazole

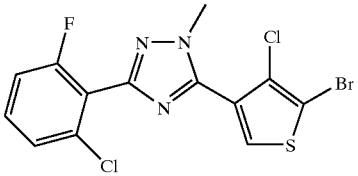

Product was isolated as a light yellow solid (51% yield): mp 111–117° C.; ¹H NMR (CDCl₃) δ 7.71 (s, 1H), 7.39–7.29 (m, 2H), 7.14–7.08 (m, 1H), 3.97 (s, 3H); EI/MS 407 m/e (M⁺); Calcd for C₁₃H₇BrCl₂FN₃S: C, 38.36; H, 1.73; N, 10.32; Found: C, 38.57; H, 1.71; N, 10.18.

Example H 3-(2-Chloro-6-fluorophenyl)-5-(4-bromo-3,5-dimethylthien-2-yl)-1-methyl-1H-1,2,4-triazole

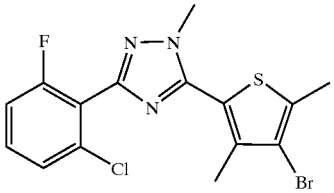

n-Butyllithium (0.7 g, 10.8 mmol) was added dropwise to a solution of 5-(4,5-dibromo-3-methylthien-2-yl)-3-(2-chloro-6-fluorophenyl)-1-methyl-1H-1,2,4-triazole (5 g, 10.8 mmol) in THF (70 mL) at −70° C. and stirred for 1 hour. Iodomethane (1.6 g, 11.29 mmol) was added to the reaction mixture and allowed to warm to 25° C. After adding saturated aq ammonium chloride (10 mL), the organic layer was separated, washed with water, followed by saturated aq sodium chloride (20 mL) and dried over sodium sulfate, filtered, and concentrated. The residue was chromatographed to give the product as a yellow oil (2.0 g, 47%): $^1$H NMR (CDCl$_3$) δ 2.32 (s, 3H), 2.48 (s, 3H), 3.99 (s, 3H), 7.07–7.13 (m, 1H), 7.28–7.38 (m, 2H); EI/MS 400 m/e (M$^+$); Calcd. for C$_{15}$H$_{12}$ClBrFN$_3$S: C, 44.96; H, 3.02; N, 10.49; Found: C, 44.94; H, 3.01; N, 10.29.

Example I

2-Fluoro-4-trifluoromethoxybenzeneboronic acid

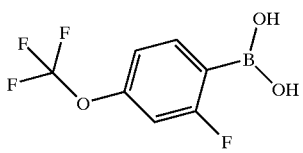

To a solution of n-butyllithium (2.5 M solution in hexanes, 14.1 mL) in THF (30 mL) at −98° C. was added a solution of 4-bromo-3-fluorotrifluoromethoxy-benzene in THF (3 mL). After stirring for 10 min. at −98° C., triisopropyl borate (4.88 mL, 3.98 g, 21 mmol) was added at a rate needed to keep the temperature below −97° C. The reaction mixture was allowed to warm to −30° C. over 30 minutes, re-cooled to −78° C. and stirred at this temperature for 30 min. Concentrated hydrochloric acid (2 mL) was added and the reaction mixture was concentrated under reduced pressure. Dilute hydrochloric acid (0.2 N, 15 mL) was added and the mixture was extracted with ether (3×20 mL). The combined ethereal layers were extracted with dilute sodium hydroxide (0.02 N, 3×30 mL). The combined aqueous extracts were cooled to 0° C., acidified to pH 3.5 using concentrated hydrochloric acid and extracted with ether (3×30 mL). The combined ethereal layers were then washed with water (15 mL) and brine (15 mL), dried over magnesium sulphate and concentrated under reduced pressure to leave 2.3 g of yellow solid. Recrystallisation from hexane afforded pink needles (1.25 g, 41%): mp 89–93° C.; $^1$H NMR (CDCl$_3$) δ 7.89 (t, 1H), 7.07 (d, 1H), 6.94 (d, 1H), 5.11 (d, 2H); EI/MS 223 m/e (M−1).

The following compounds were prepared according to the general procedure of Example I.

2-Fluoro-4-trifluoromethylbenzeneboronic acid

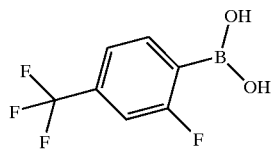

Product was isolated as a yellow solid (30% yield): mp 115–116° C.; $^1$H NMR (CDCl$_3$) δ 7.98 (t, 1H), 7.47 (d, 1H), 7.32 (d, 1H), 5.11 (d, 1H); EI/MS 207 m/e (M−1); IR (liq film) 1331 cm$^{-1}$.

2-Fluoro-5-trifluoromethylbenzeneboronic acid

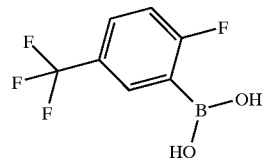

Product was isolated as iridescent plates (24% yield): $^1$H NMR (CDCl$_3$) δ 7.61 (m, 1H), 7.51 (m, 1H), 7.04 (m, 1H), 5.11 (d, 1H); EI/MS 207 m/e (M−1); IR (liq film) 1361 cm$^{-1}$; Calcd. for C$_7$H$_5$BF$_4$O$_2$: C, 40.44; H, 2.42; Found: C, 39.79; H, 2.33.

Example J 4-(4,4,5,5-Tetramethyl-1,3,2-dioxaborolan-2-yl)-1,1,2,2-tetrafluoroethoxybenzene

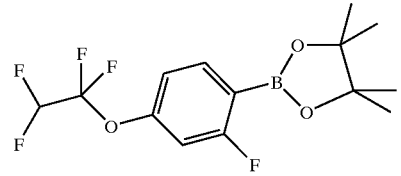

Triethylamine (4.59 mL, 3.33 g, 33 mmol) and 4-(1,1,2,2-tetrafluoroethoxy)-bromobenzene (3 g, 11 mmol) were added to a suspension of 1,1'-bis-[diphenylphosphino]ferrocenedichloropalladium (II) in dry dioxane (45 mL). Neat 4,4,5,5-tetramethyl-1,3,2-dioxaborane (2.39 mL, 2.11 g, 16 mmol) was then added to this mixture and refluxed for three days. After cooling to room temperature, the reaction mixture was poured into water (300 mL) and extracted with ether (3×100 mL). The combined ethereal extracts were washed with water (150 mL) and brine (70 mL), dried over magnesium sulphate, concentrated under reduced pressure and distilled at 0.06 mm Hg (99° C.) to afford the product (1.88 g, 53%) as a yellow oil: $^1$H NMR (CDCl$_3$) δ 7.83 (d, 2H), 7.20 (d, 2H), 6.08, 5.90 & 5.72 (tt, 1H), 1.34 (s, 12H); EI/MS 320 m/e (M$^+$); IR (liq film) 1364 cm$^{-1}$.

Example 1

3-(2-Chloro-6-fluorophenyl)-5-[4-methyl-5-(4-trifluoromethoxyphenyl)thien-3-yl]-1-methyl-1H-1,2,4-triazole

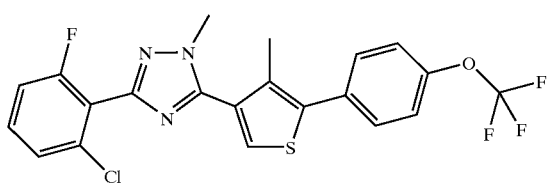

A mixture of 4-trifluoromethoxybenzeneboronic acid (0.4 g, 1.1 mmol), 3-(2-chloro-6-fluorophenyl)-5-[5-bromo-4-methylthien-3-yl]-1-methyl-1H-1,2,4-triazole (0.4 g, 1 mmol), sodium carbonate (0.2 g, 1.9 mmol), tri-o-tolylphosphine (32 mg, 0.1 mmol) and dichlorobis(triphenylphosphine)palladium(II) (73 mg, 0.1 mmol) were refluxed under nitrogen for 16 hours in an acetonitrile (14 mL) and water (1.4 mL) solution. After cooling to room temperature, the reactants were poured into dilute hydrochloric acid (1 N, 50 mL) and extracted with ether (3×50 mL). The combined ethereal extracts were washed with water (100 mL), saturated aqueous bicarbonate (70 mL) and brine (50 mL), dried over magnesium sulphate, filtered and concentrated. The residue was chromatographed over silica to afford the product as a yellow gum (210 mg, 43%): $^1$H NMR (CDCl$_3$) δ 7.55 (s, 1H), 7.49 (d, 2H), 7.28–7.39 (m, 4H), 7.11 (t, 1H), 4.03 (s, 3H), 2.33 (s, 3H); EI/MS 467 m/e (M−1).

The following compounds were prepared according to the general procedure of Example 1.

3-(2-Chloro-6-fluorophenyl)-5-{4-chloro-5-[4-(trifluoromethoxy)phenyl]thien-3-yl}-1-methyl-1H-1,2,4-triazole

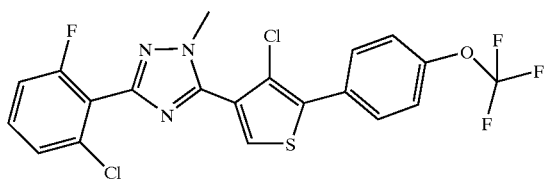

Product was isolated as a white solid: mp 112–116° C.; $^1$H NMR (CDCl$_3$) δ 7.72 (t, 3H, J=4.3 Hz), 7.40–7.30 (m, 4H), 7.15–7.09 (m, 1H), 4.09 (s, 3H); EI/MS 487 m/e (M$^+$); Calcd for C$_{20}$H$_{11}$Cl$_2$F$_4$N$_3$OS: C, 49.20; H, 2.27; N, 8.61; Found: C, 48.95; H, 2.24; N, 8.48.

3-(2-Chloro-6-fluorophenyl)-5-{4-chloro-5-[4-(trifluoromethyl)phenyl]thien-3-yl}-1-methyl-1H-1,2,4-triazole

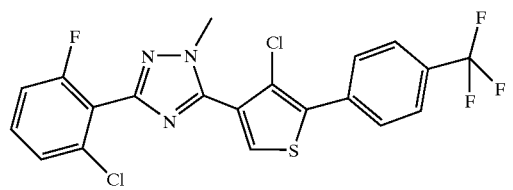

Product was isolated as a white solid (66% yield): mp 88–92° C.; $^1$H NMR (CDCl$_3$) δ 7.82 (d, 2H, J=8.0 Hz), 7.76 (s, 1H), 7.74 (d, 2H, J=8.0 Hz), 7.40–7.30 (m, 2H), 7.15–7.09 (m, 1H), 6.96–6.92 (m, 1H), 4.02 (m, 3H); EI/MS 471 m/e (M$^+$); Calcd for C$_{20}$H$_{11}$Cl$_2$F$_4$N$_3$S: C, 50.86; H, 2.35; N, 8.90; Found: C, 50.81; H, 2.39; N, 8.77.

3-(2-Chloro-6-fluorophenyl)-5-[4-chloro-5-(4-ethoxyphenyl)thien-3-yl]-1-methyl-1H-1,2,4-triazole

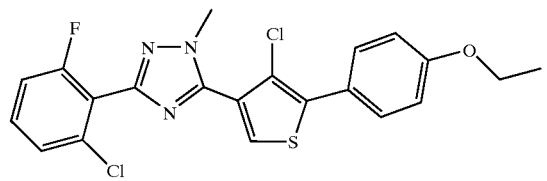

Product was isolated as a light yellow solid (77% yield): mp 120–128° C.; $^1$H NMR (CDCl$_3$) δ 7.63–7.58 (m, 3H), 7.39–7.29 (m, 2H), 7.14–7.08 (m, 1H), 7.01–6.96 (m, 2H), 4.09 (q, 2H, J=6.9 Hz), 4.00 (s, 3H), 1.45 (t, 3H, J=6.9 Hz); EI/MS 447 m/e (M$^+$).

3-(2,6-Difluorophenyl)-5-[5-(4-trifluoromethoxyphenyl)thien-3-yl]-1-methyl-1H-1,2,4-triazole

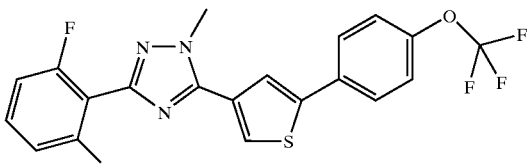

Product was isolated as a yellowish solid (37% yield): mp 88–91° C.; $^1$H NMR (CDCl$_3$) δ 7.75 (d, 1H), 7.72 (d, 1H), 7.67 (d, 2H), 7.36–7.43 (m, 1H), 7.02 (t, 1H), 4.17 (s, 3H); EI/MS 437 m/e (M$^+$).

3-(2-Chloro-6-fluorophenyl)-5-[5-(4-trifluoromethoxyphenyl)thien-3-yl]-1-methyl-1H-1,2,4-triazole

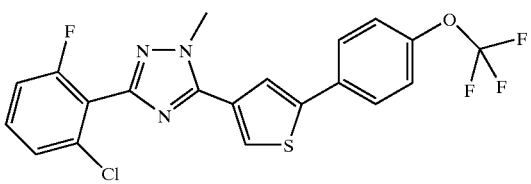

Product was isolated as a yellow solid (88% yield): mp 124–125° C.; $^1$H NMR (CDCl$_3$) δ 7.77 (d, 1H), 7.74 (d, 1H), 7.67 (d, 2H), 7.25–7.40 (m, 4H), 7.11 (t, 1H), 4.19 (s, 3H); EI/MS: 453 m/e (M−1); Calcd. for C$_{20}$H$_{12}$ClF$_4$N$_3$OS: C, 52.9; H, 2.67; N, 9.26; S, 7.06; Found: C, 53.1; H, 2.67; N, 8.7; S, 7.0.

3-(2-Chloro-6-fluorophenyl)-5-[5-(2-fluoro-4-trifluoromethoxyphenyl)thien-3-yl]-1-methyl-1H-1,2,4-triazole

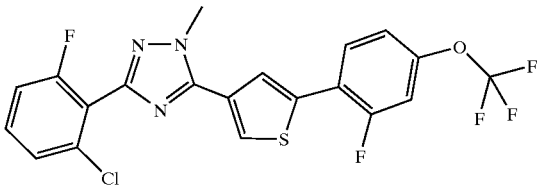

Product was isolated as an amorphous white solid (32% yield): mp 121° C.; $^1$H NMR (CDCl$_3$) δ 8.02 (s, 1H), 7.89 (s, 1H), 7.82 (t, 1H), 7.47 (s, 1H), 7.43 (d, 1H), 7.29–7.39 (m, 2H), 7.11 (t, 1H), 4.19 (s, 3H); EI/MS: 471 m/e (M−1); Calcd. for C$_{21}$H$_{15}$ClF$_5$N$_3$S: C, 53.5; H, 3.20; N, 8.90; Found: C, 53.3; H, 2.91; N, 8.91.

3-(2-Chloro-6-fluorophenyl)-5-[5-(2-fluoro-4-methylphenyl)thien-3-yl]-1-methyl-1H-1,2,4-triazole

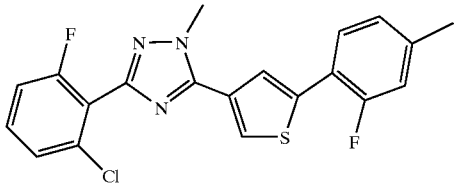

Product was isolated as yellow prisms (32% yield): mp 128–129° C.; $^1$H NMR (CDCl$_3$) δ 7.86 (d, 1H), 7.79 (d, 1H), 7.55 (t, 1H), 7.28–7.39 (m, 2H), 7.11 (t, 1H), 4.17 (s, 3H), 2.38 (s, 3H); EI/MS 402 m/e (M$^+$); Calcd. for C$_{20}$H$_{14}$ClF$_2$N$_3$S: C, 59.8; H, 3.51; N, 10.5; Found: C, 59.6; H, 3.44; N, 10.3.

3-(2-Chloro-6-fluorophenyl)-5-[5-(4-ethoxyphenyl)thien-3-yl]-1-methyl-1H-1,2,4-triazole

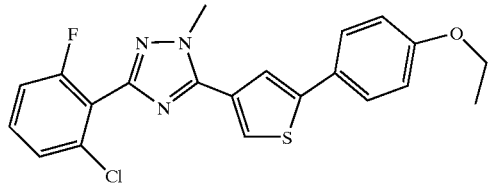

Product was isolated as yellowish crystals (56% yield): mp 113–114° C.; $^1$H NMR (CDCl$_3$) δ 7.66 (d, 1H), 7.65 (d, 1H), 7.56 (d, 2H), 7.29–7.39 (m, 2H), 7.10 (t, 1H), 4.17 (s, 3H), 4.07 (q, 2H), 1.44 (t, 3H); EI/MS 413 m/e (M−1); Calcd. for C$_{21}$H$_{17}$ClFN$_3$SO: C, 60.9; H, 4.14; N, 10.2; S, 7.75; Found: C, 60.7; H, 4.16; N, 9.93; S, 7.61.

3-(2-Chloro-6-fluorophenyl)-5-[5-(3-trifluoromethylphenyl)thien-3-yl]-1-methyl-1H-1,2,4-triazole

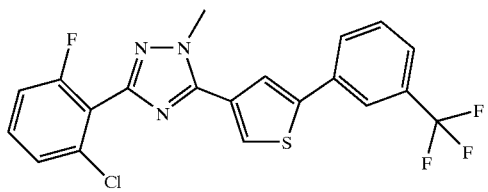

Product was isolated as a yellow gum (66% yield): $^1$H NMR (CDCl$_3$) δ 7.82 (d, 1H), 7.88 (d, 2H), 7.82 (d, 2H), 7.78 (d, 1H), 7.53–7.58 (m, 2H), 7.34–7.38 (m, 2H), 7.11 (t, 1H), 4.20 (s, 3H); EI/MS 437 m/e (M−1); Calcd. for C$_{20}$H$_{12}$ClF$_4$N$_3$S: C, 54.9; H, 2.76; N, 9.60; Found: C, 55.2; H, 2.94; N, 9.60.

3-(2,6-Difluorophenyl)-5-[5-(4-trifluoromethylphenyl)thien-3-yl]-1-methyl-1H-1,2,4-triazole

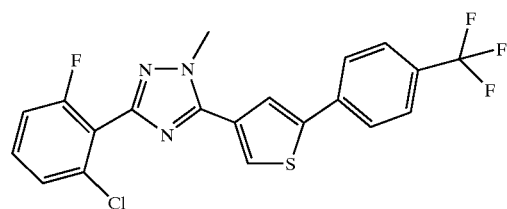

Product was isolated as a yellow solid (37% yield): mp 143–146° C.; $^1$H NMR (CDCl$_3$) δ 7.88 (d, 1H), 7.77 (d, 1H), 7.75 (d, 2H), 7.66 (d, 2H), 7.33–7.43 (m, 1H), 7.05 (t, 1H), 4.17 (s, 3H); EI/MS 421 m/e (M$^+$).

3-(2-Chloro-6-fluorophenyl)-5-[5-(4-trifluoromethylphenyl)thien-3-yl]-1-methyl-1H-1,2,4-triazole

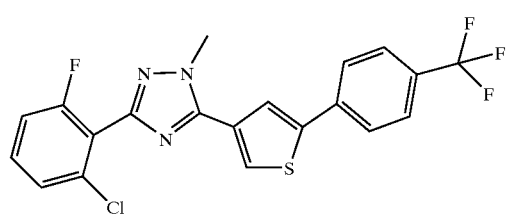

Product was isolated as a yellow solid (80% yield): mp 166° C.; $^1$H NMR (CDCl$_3$) δ 7.88 (d, 1H), 7.78 (d, 1H), 7.75 (d, 2H), 7.66 (d, 2H), 7.29–7.40 (m, 2H), 7.11 (t, 1H), 4.19 (s, 3H); EI/MS 437 m/e (M−1).

3-(2-Chloro-6-fluorophenyl)-5-[2-chloro-5-(2,3-dihydro-1-benzofuran-5-yl)thien-3-yl]-1-methyl-1H-1,2,4-triazole

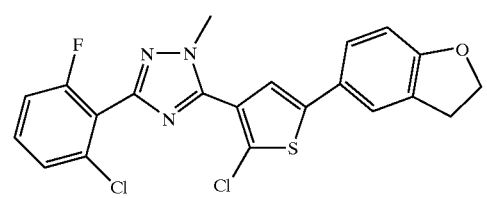

Product was isolated as a yellowish amorphous solid (21% yield): mp 180° C.; $^1$H NMR (CDCl$_3$) δ 7.29–7.40 (m, 2H), 7.26 (s, 1H), 7.10–7.14 (m, 2H), 6.89 (d, 1H), 4.04 (s, 3H), 3.93 (s, 3H), 3.92 (s, 3H); EI/MS 446 m/e (M$^+$); Calcd. for C$_{21}$H$_{16}$Cl$_2$FN$_3$OS: C, 54.3; H, 3.47; N, 9.05; Found: C, 54.1; H, 3.52; N, 8.76.

3-(2-Chloro-6-fluorophenyl)-5-[2-chloro-5-(4-ethoxyphenyl)thien-3-yl]-1-methyl-1H-1,2,4-triazole

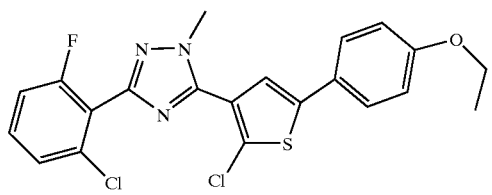

Product was isolated as a white solid (10% yield): mp 172° C.; $^1$H NMR (CDCl$_3$) δ 7.45 (d, 2H), 7.29–7.39 (m, 2H), 7.23 (s, 1H), 7.11 (m, 1H), 6.91 (d, 1H), 4.06 (q, 2H), 4.03 (s, 3H), 1.44 (t, 3H); EI/MS 448 m/e (M$^+$).

3-(2-Chloro-6-fluorophenyl)-5-[2-methyl-5-(4-trifluoromethylphenyl)thien-3-yl]-1-methyl-1H-1,2,4-triazole

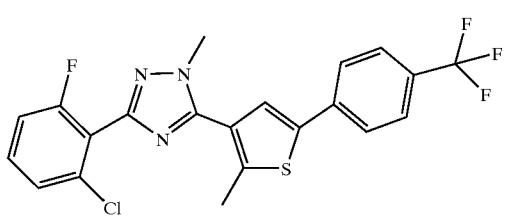

Product was isolated as white cubes (62% yield): mp 167–168° C.; $^1$H NMR (CDCl$_3$) δ 7.67 (d, 2H), 7.65 (d, 2H), 7.42 (s, 1H), 7.29–7.39 (m, 2H), 7.11 (m, 1H), 4.01 (s, 3H), 2.64 (s, 3H); EI/MS 452 m/e (M$^+$); Calcd. for C$_{21}$H$_{14}$ClF$_4$N$_3$S: C, 55.8; H, 3.12; N, 9.30; Found: C, 55.9; H, 3.27; N, 9.32.

3-(2-Chloro-6-fluorophenyl)-5-[2-methyl-5-(4-ethoxyphenyl)thien-3-yl]-1-methyl-1H-1,2,4-triazole

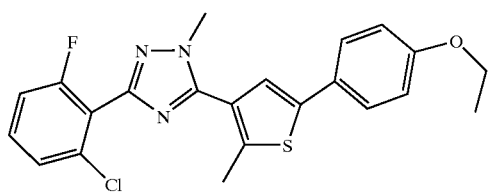

Product was isolated as white needles (75% yield): mp 184–185° C.; $^1$H NMR (CDCl$_3$) δ 7.48 (d, 2H), 7.28–7.38 (m, 2H), 7.20 (s, 1H), 7.20 (s, 1H), 7.10 (m, 1H), 6.91 (d, 2H), 4.06 (q, 2H), 4.00 (s, 3H), 2.60 (s, 3H), 1.44 (t, 3H); EI/MS 428 m/e (M$^+$); Calcd. for C$_{21}$H$_{14}$ClF$_4$N$_3$S: C, 55.8; H, 3.12; N, 9.30; Found: C, 55.9; H, 3.27; N, 9.32.

3-(2-Chloro-6-fluorophenyl)-5-[2-methyl-5-(3-trifluoromethoxyphenyl)thien-3-yl]-1-methyl-1H-1,2,4-triazole

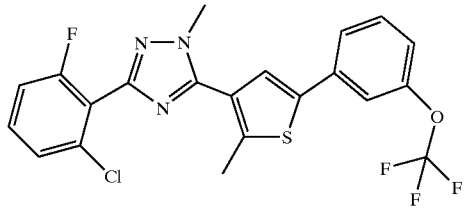

Product was isolated as iridescent flakes (52% yield): mp 124–125° C.; $^1$H NMR (CDCl$_3$) δ 7.29–7.52 (m, 6H), 7.08–7.18 (m, 2H); EI/MS 468 m/e (M$^+$); Calcd. for C$_{21}$H$_{14}$ClF$_4$N$_3$OS: C, 53.9; H, 3.02; N, 8.98; Found: C, 53.8; H, 2.90; N, 8.87.

3-(2-Chloro-6-fluorophenyl)-5-[5-(2-fluoro-4-methylphenyl)-2-methylthien-3-yl]-1-methyl-1H-1,2,4-triazole

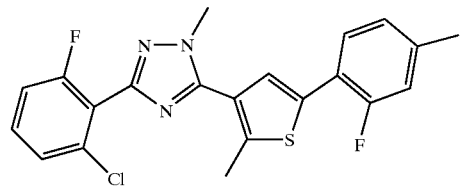

Product was isolated as iridescent plates (17% yield): mp 168–169° C.; $^1$H NMR (CDCl$_3$) δ 7.447.49 (m, 2H), 7.29–7.38 (m, 2H), 7.10 (m, 1H), 6.97 (s, 1H), 6.96 (d, 1H), 4.01 (s, 3H), 2.64 (s, 3H), 2.37 (s, 3H); EI/MS 416 m/e (M$^+$).

3-(2-Chloro-6-fluorophenyl)-5-[5-(3,4-dichlorophenyl)-2-methylthien-3-yl]-1-methyl-1H-1,2,4-triazole

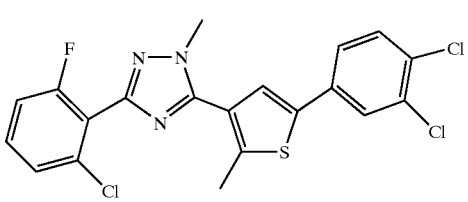

Product was isolated as an amorphous white solid (28% yield): mp 162–163° C.; $^1$H NMR (CDCl$_3$) δ 7.65 (d, 1H), 7.45 (d, 1H), 7.29–7.40 (m, 4H), 7.11 (m, 1H), 4.01 (s, 3H), 2.62 (s, 3H); EI/MS 454 m/e (M+1); Calcd. for C$_{20}$H$_{13}$Cl$_2$FN$_3$S: C, 53.1; H, 2.81; N, 9.28; Found: C, 53.1; H, 2.93; N, 9.12.

3-(2-Chloro-6-fluorophenyl)-5-[5-(4-chloro-2-fluorophenyl)-2-methylthien-3-yl]-1-methyl-1H-1,2,4-triazole

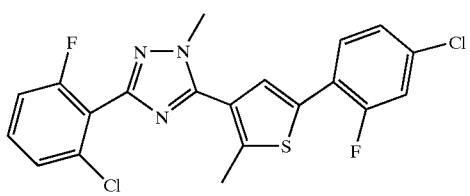

Product was isolated as iridescent plates (39% yield): mp 177–178° C.; $^1$H NMR (CDCl$_3$) δ 7.60 (dd, 1H), 7.40–7.45 (m, 1H), 7.27–7.38 (m, 3H), 7.08–7.20 (m, 2H), 4.01 (s, 3H), 2.62 (s, 3H); EI/MS 436 m/e (M$^+$); Calcd. for C$_{20}$H$_{13}$Cl$_2$F$_2$N$_3$S: C, 55.1; H, 3.00; N, 9.63; Found: C, 54.8; H, 3.07; N, 9.46.

3-(2-Chloro-6-fluorophenyl)-5-[5-(2-fluoro-4-trifluoromethylphenyl)-2-methylthien-3-yl]-1-methyl-1H-1,2,4-triazole

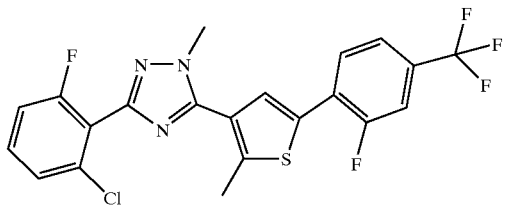

Product was isolated as colorless needles (14% yield): mp 153–154° C.; $^1$H NMR (CDCl$_3$) δ 7.71 (t, 1H), 7.61 (s, 1H), 7.42–7.46 (m, H), 7.29–7.39 (m, 2H), 7.11 (m, 1H), 4.02 (s, 3H), 2.66 (s, 3H); EI/MS 470 m/e (M$^+$).

3-(2-Chloro-6-fluorophenyl)-5-[5-(2-fluoro-5-trifluoromethylphenyl)-2-methylthien-3-yl]-1-methyl-1H-1,2,4-triazole

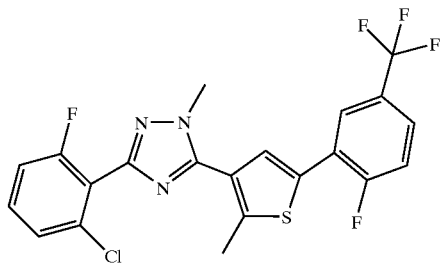

Product was isolated as a white solid (27% yield): mp 141–142° C.; $^1$H NMR (CDCl$_3$) δ 7.86 (dd, 1H), 7.58 (s, 1H), 7.56 (m, 1H), 7.28–7.39 (m, 3H), 7.11 (m, 1H), 4.02 (s, 3H), 2.66 (s, 3H); EI/MS 470 m/e (M+2); Calcd. for C$_{21}$H$_{13}$ClF$_5$N$_3$S: C, 53.7; H, 2.79; N, 8.94; Found: C, 53.5; H, 2.85; N, 8.94.

3-(2-Chloro-6-fluorophenyl)-5-[2-chloro-5-(4-ethoxyphenyl)thien-3-yl-1-methyl-1H-1,2,4-triazole

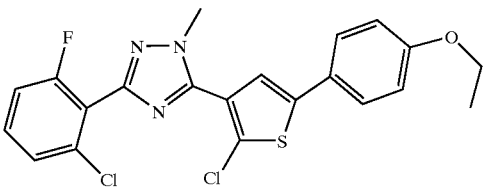

Product was isolated as an amorphous, white solid (14% yield): mp 153–155° C.; $^1$H NMR (CDCl$_3$) δ 7.44 (d, 2H), 7.29–7.39 (m, 2H), 7.22 (s, 1H), 7.11 (t, 1H), 6.90 (d, 2H), 4.03–4.09 (m, 5H), 1.43 (t, 3H); EI/MS 450 m/e (M+2); Calcd. for C$_{22}$H$_{19}$ClFN$_3$OS: C, 61.8; H, 4.48; N, 9.82; Found: C, 61.4; H, 4.42; N, 9.71.

3-(2-Chloro-6-fluorophenyl)-5-[4-methyl-5-(4-trifluoromethylphenyl)thien-3-yl]-1-methyl-1H-1,2,4-triazole

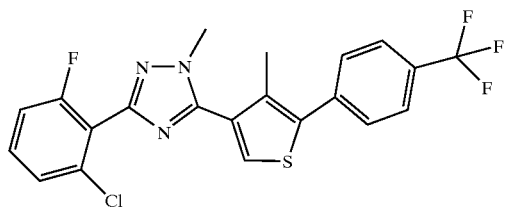

Product was isolated as a yellow gum (38% yield): $^1$H NMR (CDCl$_3$) δ 7.71 (d, 2H), 7.60 (d, 2H), 7.59 (s, 1H), 7.30–7.40 (m, 2H), 7.11 (t, 1H), 4.04 (s, 3H), 2.36 (s, 3H); EI/MS 451 m/e (M−1).

3-(2-Chloro-6-fluorophenyl)-5-[5-(4-chlorophenyl)-4-methylthien-3-yl]-1-methyl-1H-1,2,4-triazole

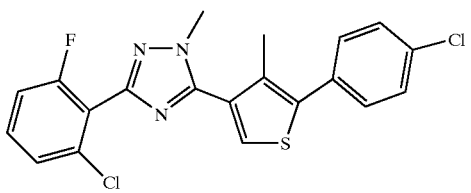

Product was isolated as a sticky, yellow foam (30% yield): $^1$H NMR (CDCl$_3$) δ 7.54 (s, 1H), 7.38–7.41 (m, 4H), 7.29–7.35 (m, 2H), 7.11 (t, 1H), 4.03 (s, 3H), 2.32 (s, 3H); EI/MS 417 m/e (M−1).

3-(2-Chloro-6-fluorophenyl)-5-[4-methyl-5-(4-ethoxyphenyl)thien-3-yl]-1-methyl-1H-1,2,4-triazole

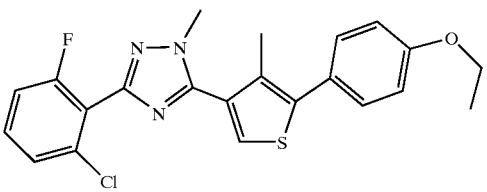

Product was isolated as white needles (50% yield): mp 131–132° C.; $^1$H NMR (CDCl$_3$) δ 7.47 (s, 1H), 7.38 (d, 4H), 7.29 7.36 (m, 2H), 7.11 (t, 1H), 6.96 (d, 2H), 4.08 (q, 2H), 4.02 (s, 3H), 2.30 (s, 3H), 1.45 (t, 3H); EI/MS 427 m/e (M−1).

3-(2-Chloro-6-fluorophenyl)-5-[5-(4-methoxyphenyl)-4-methylthien-3-yl]-1-methyl-1H-12.4-triazole

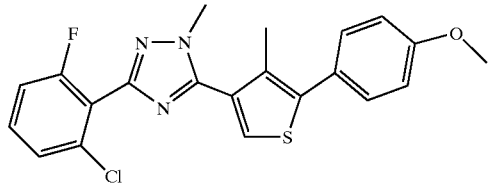

Product was isolated as a yellow glass (30% yield): ¹H NMR (CDCl₃) δ 7.48 (s, 1H), 7.41 (d, 2H), 7.29–7.38 (m, 2H), 7.11 (t, 1H), 6.98 (d, 2H), 4.03 (s, 3H), 3.85 (s, 3H), 2.31 (s, 3H); EI/MS 413 m/e (M−1).

3-(2-Chloro-6-fluorophenyl)-5-[4-methyl-5-(4-methylphenyl)thien-3-yl]-1-methyl-1H-1,2,4-triazole

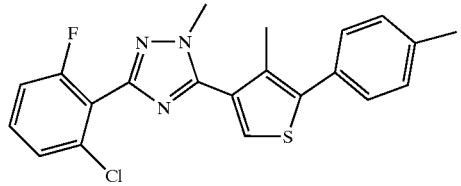

Product was isolated as an off-white solid (39% yield): mp 158–159° C.; ¹H NMR (CDCl₃) δ 7.50 (s, 1H), 7.29–7.39 (m, 4H), 7.27 (d, 2H), 7.11 (t, 1H), 4.03 (s, 3H), 2.32 (s, 3H); EI/MS 397 m/e (M−1).

3-(2-Chloro-6-fluorophenyl-5-[4-methyl-5-(3-trifluoromethoxyphenyl)thien-3-yl]-1-methyl-1H-1,2,4-triazole

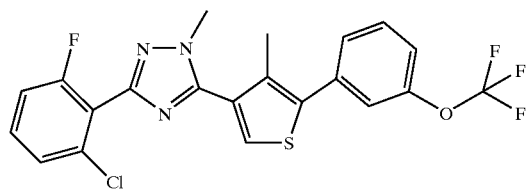

Product was isolated as a yellowish solid (16% yield): mp 133° C.; ¹H NMR (CDCl₃) δ 7.57 (s, 1H), 7.30–7.51 (m, 6H), 7.11 (t, 1H), 4.04 (s, 3H), 2.34 (s, 3H); EI/MS 467 m/e (M−1).

3-(2-Chloro-6-fluorophenyl)-5-[4-methyl-5-(3-trifluoromethylphenyl)thien-3-yl]-1-methyl-1H-1,24-triazole

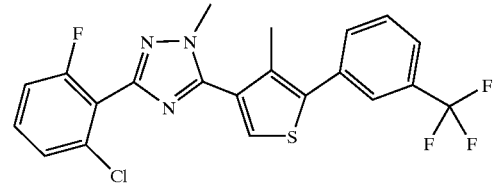

Product was isolated as free-flowing cubes (48% yield): mp 134–135° C.; ¹H NMR (CDCl₃) δ 7.73 (br s, 1H), 7.55–7.67 (m, 4H), 7.29–7.39 (m, 2H), 7.11 (t, 1H), 4.04 (s, 3H), 2.34 (s, 3H); EI/MS 451 m/e (M−1); Calcd. for C₂₁H₁₄ClF₄N₃S: C, 55.9; H, 3.13; N, 9.31; S, 7.09; Found: C, 55.8; H, 3.26; N, 9.26; S, 7.16.

3-(2-Chloro-6-fluorophenyl)-5-[5-(3-ethoxyphenyl)-4-methylthien-3-yl]-1-methyl-1H-1,2,4-triazole

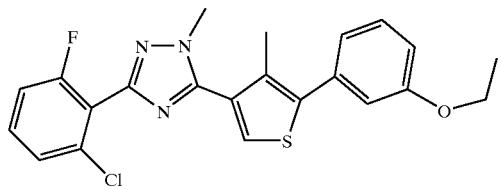

Product was isolated as a yellow solid (65% yield): mp 98–99° C.; ¹H NMR (CDCl₃) δ 7.51 (s, 1H), 7.26–7.39 (m, 3H), 7.00–7.14 (m, 2H), 6.92 (dd, 1H), 4.07 (q, 2H), 4.02 (s, 3H), 2.34 (s, 3H), 1.43 (t, 3H); EI/MS 427 m/e (M−1).

3-(2-Chloro-6-fluorophenyl)-5-[4-methyl-5-(4-methylthiophenyl)thien-3-yl]-1-methyl-1H-1,2,4-triazole

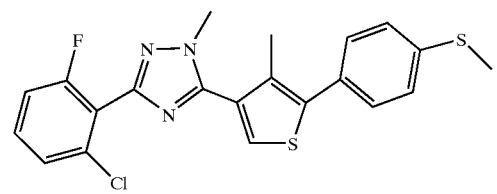

Product was isolated as a white, fluffy solid (74% yield): mp 163–164° C.; ¹H NMR (CDCl₃) δ 7.51 (s, 1H), 7.40 (d, 2H), 7.29–7.37 (m, 4H), 7.11 (t, 1H), 4.03 (s, 3H), 2.53 (s, 3H), 2.32 (s, 3H); EI/MS 429 m/e (M−1).

3-(2-Chloro-6-fluorophenyl)-5-[4-methyl-5-(4-phenoxyphenyl)thien-3-yl-1-methyl-1H-12,4-triazole

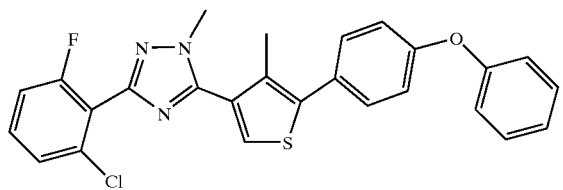

Product was isolated as a yellow foam (51% yield): ¹H NMR (CDCl₃) δ 7.50 (s, 1H), 7.29–7.45 (m, 6H), 7.04–7.17 (m, 6H), 4.03 (s, 3H), 2.33 (s, 3H); EI/MS 475 m/e (M−1).

3-(2-Chloro-6-fluorophenyl)-5-[4-methyl-5-(4-isopropyl)phenylthien-3-yl]-1-methyl-1H-1,2,4-triazole

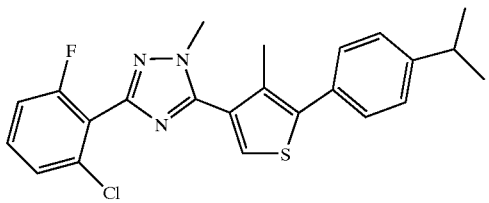

Product was isolated as needles (15% yield): mp 143–144° C.; ¹H NMR (CDCl₃) δ 7.49 (s, 1H), 7.41 (d, 2H), 7.29–7.37 (m, 4H), 7.11 (m, 1H), 4.03 (s, 3H), 2.96 (pentet, 1H), 2.33 (s, 3H), 1.29 (d, 6H); EI/MS 426 m/e (M⁺).

3-(2-Chloro-6-fluorophenyl)-5-{5-[(3-fluorophenyl)-4-methyl]thien-3-yl}-1-methyl-1H-1,2,4-triazole

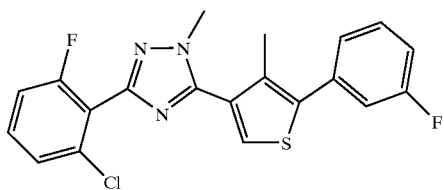

Product was isolated as an amorphous white solid (89% yield): mp 143–144° C.; ¹H NMR (CDCl₃) δ 7.55 (s, 1H), 7.04–7.44 (m, 7H), 4.02 (s, 3H), 2.35 (s, 3H); EI/MS 402 m/e (M⁺); Calcd. for C₂₀H₁₄ClF₂N₃S: C, 59.8; H, 3.5; N, 10.5; Found: C, 59.8; H, 3.56; N, 10.3.

3-(2-Chloro-6-fluorophenyl)-5-{4-methyl-5-[4-(tetrahydro-2H-pyran-2-yloxy)phenyl]thien-3-yl}-1-methyl-1H-1,2,4-triazole

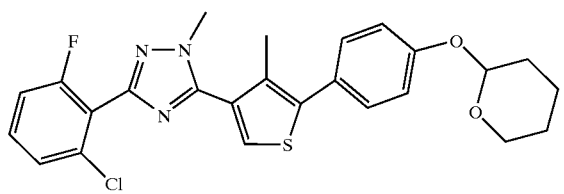

Product was isolated as a white solid (72% yield): mp 185–186° C.; ¹H NMR (CDCl₃) δ 7.49 (s, 1H), 7.44 (d, 2H), 7.29–7.38 (m, 2H), 7.09–7.18 (m, 3H), 5.49 (m, 1H), 3.88–3.97 (m, 1H), 4.03 (s, 3H), 3.62–3.68 (m, 1H), 2.35 (s, 3H), 1.98–2.07 (m, 1H), 1.87–1.91 (m, 2H), 1.60–1.73 (m, 3H); EI/MS 484 m/e (M⁺); Calcd. for C₂₀H₁₄ClF₂N₃S: C, 59.8; H, 3.5; N, 10.5; Found: C, 59.8; H, 3.56; N, 10.3.

3-(2-Chloro-6-fluorophenyl)-5-[5-(3,4-difluorophenyl)-4-methylthien-3-yl]-1-methyl-1H-1,2,4-triazole

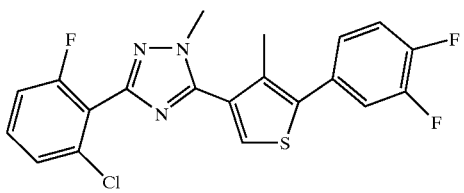

Product was isolated as white cubes (28% yield): mp 93° C.; ¹H NMR (CDCl₃) δ 7.54 (s, 1H), 7.28–7.37 (m, 3H), 7.19–7.25 (m, 2H), 7.11 (t, 1H), 4.03 (s, 3H), 2.32 (s, 3H); EI/MS 419 (M−1).

3-(2-Chloro-6-fluorophenyl)-5-[5-(3-chloro-4-methylphenyl)-4-methylthien-3-yl]-1-methyl-1H-1,2,4-triazole

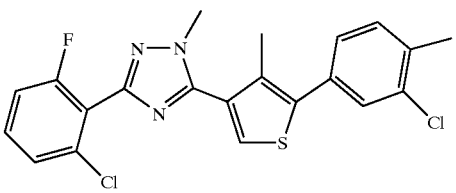

Product was isolated as white micro-needles (53% yield): mp 136–137° C.; ¹H NMR (CDCl₃) δ 7.53 (s, 1H), 7.46 (s, 1H), 7.27–7.37 (m, 4H), 7.11 (t, 1H), 4.02 (s, 3H), 2.42 (s, 3H), 2.32 (s, 3H); EI/MS 432 m/e (M⁺); Calcd. for C₂₁H₁₆Cl₂FN₃S: C, 58.3; H, 3.73; N, 9.7; S, 7.4; Found: C, 58.0; H, 3.72; N, 9.43; S, 7.22.

3-(2-Chloro-6-fluorophenyl)-5-[5-(3-chloro-2-trifluoromethylphenyl)-4-methylthien-3-yl]-1-methyl-1H-12.4-triazole

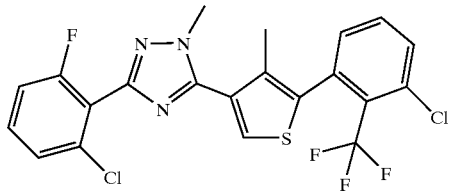

Product was isolated as a yellowish foam (15% yield): ¹H NMR (CDCl₃) δ 7.78 (d, 1H), 7.65 (s, 1H), 7.58 (d, 1H), 7.45 (s, 1H), 7.29–7.39 (m, 2H), 7.11 (t, 1H), 4.05 (s, 3H), 2.14 (s, 3H); EI/MS 485 m/e (M−1).

3-(2-Chloro-6-fluorophenyl)-5-[5-(4-chloro-3-trifluoromethylphenyl)-4-methylthien-3-yl]-1-methyl-1H-12.4-triazole

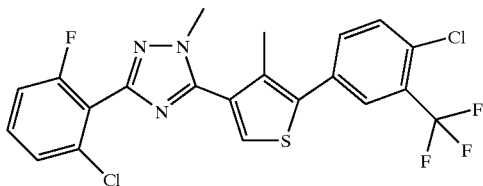

Product was isolated as a colourless glass (8% yield): $^1$H NMR (CDCl$_3$) δ 7.79 (s, 1H), 7.58 (m, 1H), 7.29–7.39 (m, 2H), 7.11 (t, 1H), 4.03 (s, 3H), 2.33 (s, 3H); EI/MS 485 m/e (M−1).

3-(2-Chloro-6-fluorophenyl)-5-[5-(2-fluoro-4-trifluoromethylphenyl)-4-methylthien-3-yl]-1-methyl-1H-1,2,4-triazole

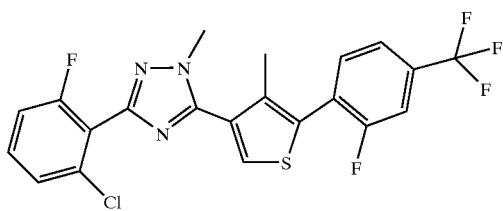

Product was isolated as a yellow glass (39% yield): $^1$H NMR (CDCl$_3$) δ 7.68 (s, 1H), 7.46–7.54 (m, 3H), 7.29–7.39 (m, 2H), 7.11 (m, 1H), 4.04 (s, 3H), 2.25 (s, 3H); EI/MS 470 (M$^+$).

3-(2-Chloro-6-fluorophenyl)-5-[5-(2-chloro-4-trifluoromethylphenyl)-4-methylthien-3-yl]-1-methyl-1H-1,2,4-triazole

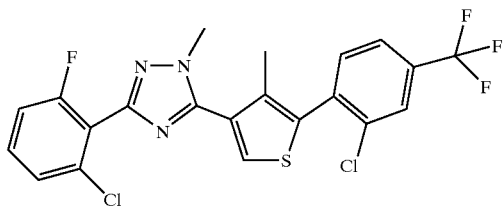

Product was isolated as an amorphous, yellowish solid (66% yield): mp 65–66° C.; $^1$H NMR (CDCl$_3$) δ 7.78 (s, 1H), 7.66 (s, 1H), 7.60 (d, 1H), 7.52 (d, 1H), 7.29–7.39 (m, 2H), 7.11 (m, 1H), 4.05 (s, 3H), 2.17 (s, 3H); EI/MS 486 m/e (M$^+$); Calcd. for C$_{21}$H$_{13}$Cl$_2$F$_4$N$_3$S: C, 51.9; H, 2.69; N, 8.64; Found: C, 51.6; H, 2.82; N, 8.45.

3-(2-Chloro-6-fluorophenyl)-5-[5-(2-fluoro-4-trifluoromethoxyphenyl)-4-methylthien-3-yl]-1-methyl-1H-1,2,4-triazole

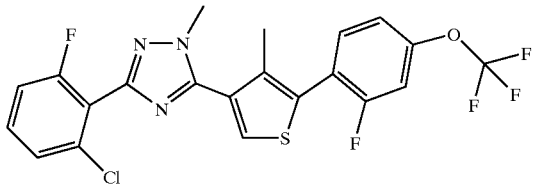

Product was isolated as a colorless gum (33% yield): $^1$H NMR (CDCl$_3$) δ 7.64 (s, 1H), 7.29–7.46 (m, 3H), 7.08–7.14 (m, 3H), 4.04 (s, 3H), 2.23 (d, 3H); EI/MS 485 m/e (M−1).

3-(2-Chloro-6-fluorophenyl)-5-F5-(2-fluoro-5-trifluoromethylphenyl)-4-methylthien-3-yl]-1-methyl-1H-1,2,4-triazole

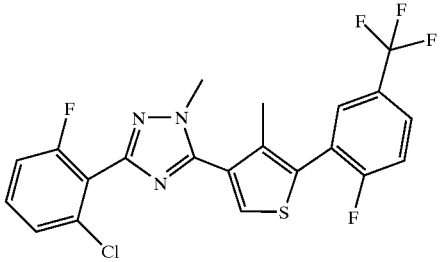

Product was isolated as a colorless glass (11% yield): $^1$H NMR (CDCl$_3$) δ 7.66–7.70 (m, 3H), 7.28–7.39 (m, 3H), 7.11 (m, 1H), 4.04 (s, 3H), 2.24 (d, 3H); EI/MS 471 m/e (M+1).

3-(2-Chloro-6-fluorophenyl)-5-[2,4-dimethyl-5-(2-fluoro-4-trifluoromethylphenyl)thien-3-yl]-1-methyl-1H-1,2,4-triazole

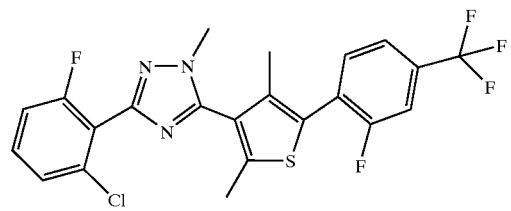

Product was obtained as a yellow semi-solid (21% yield): $^1$H NMR (CDCl$_3$) δ 7.43–7.53 (m, 3H), 7.29–7.39 (m, 2H), 7.11 (m, 1H), 3.90 (s, 3H), 2.44 (s, 3H), 2.04 (d, 3H); EI/MS 484 m/e (M$^+$).

3-(2-Chloro-6-fluorophenyl)-5-[2,4-dimethyl-5-(4-trifluoromethylphenyl)thien-3-yl]-1-methyl-1H-1,2,4-triazole

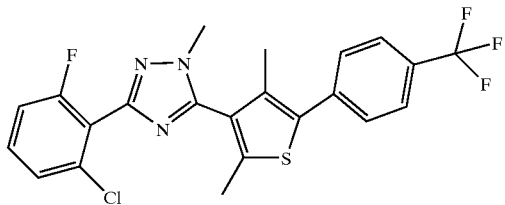

Product was isolated as a white solid (5% yield): mp 146–147° C.; $^1$H NMR (CDCl$_3$) δ 7.67 (d, 2H), 7.56 (d, 2H), 7.29–7.39 (m, 2H), 7.12 (m, 1H), 3.90 (s, 3H), 2.43 (s, 3H), 2.16 (d, 3H); EI/MS 466 m/e (M$^+$).

3-(2-Chloro-6-fluorophenyl)-5-[2,4-dimethyl-5-(4-ethoxyphenyl)thien-3-yl]-1-methyl-1H-1,2,4-triazole

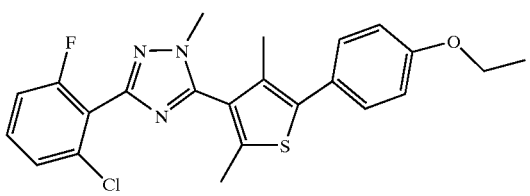

Product was isolated as white needles (41% yield): mp 148–149° C.; $^1$H NMR (CDCl$_3$) δ 7.29–7.38 (m, 4H), 7.11 (m, 1H), 6.93 (d, 2H), 4.07 (q, 2H), 3.88 (s, 3H), 2.39 (s, 3H), 2.11 (s, 3H), 1.44 (t, 3H); EI/MS 442 m/e (M$^+$); Calcd. for C$_{23}$H$_{21}$ClN$_3$OS: C, 62.4; H, 4.79; N, 9.51; Found: C, 62.4; H, 4.87; N, 9.42.

3-(2-Chloro-6-fluorophenyl)-5-[4-chloro-5-(2-fluoro-4-trifluoromethoxyphenyl)-thien-3-yl]-1-methyl-1H-1,2,4-triazole

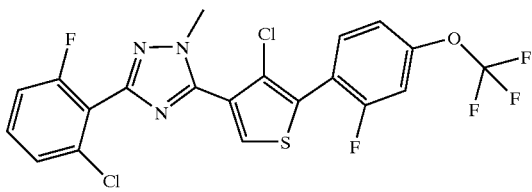

Product was obtained as a white solid (64% yield): mp 112–116° C.; $^1$H NMR (CDCl$_3$) δ 7.72 (t, J=4.3 Hz, 3H), 7.40–7.30 (m, 4H), 7.15–7.09 (m, 1H), 4.09 (s, 3H); EI/MS 487 m/e (M$^+$); Calcd. for C$_{20}$H$_{11}$Cl$_2$F$_4$N$_3$OS: C, 49.20; H, 2.27; N, 8.61; Found: C, 48.95; H, 2.24; N, 8.48.

3-(2-Chloro-6-fluorophenyl)-5-[4-chloro-5-(4-trifluoromethylphenyl)thien-3-yl]-1-methyl-1H-1,2,4-triazole

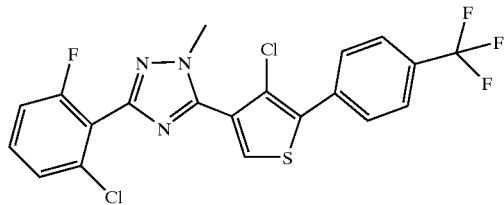

Product was isolated as a white solid (66% yield): mp 88–92° C.; $^1$H NMR (CDCl$_3$) δ 7.82 (d, J=8.0 Hz, 2H), 7.76 (s, 1H), 7.74 (d, J=8.0 Hz, 2H), 7.40–7.30 (m, 2H), 7.15–7.09 (m, 1H), 6.96–6.92 (m, 1H), 4.02 (m, 3H). EI/MS 471 m/e (M$^+$); Calcd. for C$_{20}$H$_{11}$Cl$_2$F$_4$N$_3$S: C, 50.86; H, 2.35; N, 8.90; Found: C, 50.81; H, 2.39; N, 8.77.

3-(2-Chloro-6-fluorophenyl)-5-[4-chloro-5-(4-ethoxyphenyl)thien-3-yl]-1-methyl-1H-1,2,4-triazole

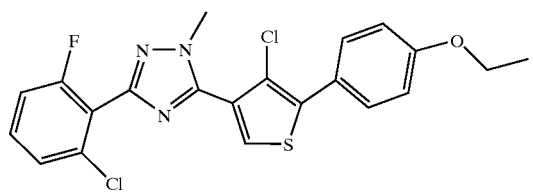

Product was isolated as a light yellow solid (77% yield): mp 120–128° C.; $^1$H NMR (CDCl$_3$) δ 7.63–7.58 (m, 3H), 7.39–7.29 (m, 2H), 7.14–7.08 (m, 1H), 7.01–6.96 (m, 2H), 4.09 (q, J=6.9 Hz, 2H), 4.00 (s, 3H), 1.45 (t, J=6.9 Hz, 3H); EI/MS 447 m/e (M$^+$).

3-(2-Chloro-6-fluorophenyl)-5-{4-methyl-5-[4-((1,1,2,2-tetrafluoroethoxy)-phenyl]thien-3-yl}-1-methyl-1H-1,2,4-triazole

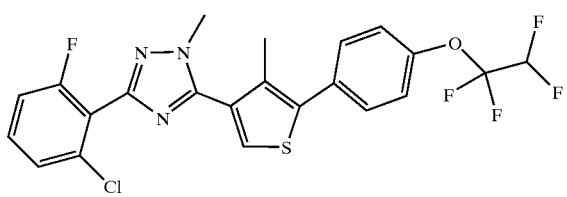

Product was isolated as a yellow gum (28% yield): $^1$H NMR (CDCl$_3$) δ 7.55 (s, 1H); 7.48 (d, 2H), 7.28–7.39 (m, 4H), 7.11 (m, 1H), 6.12, 5.94, 5.77 (tt, J=53.2 Hz, 1H), 4.03 (s, 3H), 2.33 (s, 3H); EI/MS 500 m/e (M$^+$).

3-(2-Chloro-6-fluorophenyl)-5-[5-(4-fluorophenyl)-4-methylthien-3-yl]-1-methyl-1H-1,2,4-triazole

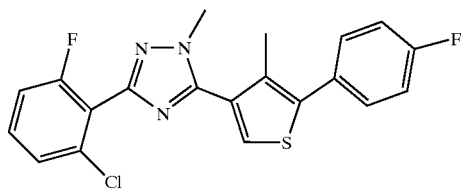

Product was isolated as a yellow solid (31% yield): mp 112–113° C.; ¹H NMR (CDCl₃) δ 7.52 (s, 1H), 7.41–7.46 (m, 2H), 7.29–7.39 (m, 2H), 7.08–7.17 (m, 3H), 4.03 (s, 3H), 2.31 (s, 3H); EI/MS 401 m/e (M−1); Calcd. for $C_{20}H_{14}ClF_2N_3S$: C, 59.8; H, 3.51; N, 10.5; Found: C, 59.6; H, 3.66; N, 10.4.

3-(2-Chloro-6-fluorophenyl)-5-[5-(4-chloro-2-fluorophenyl)-4-methylthien-3-yl]-1-methyl-1H-1,2,4-triazole

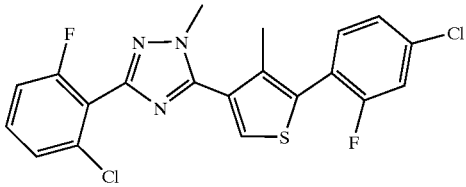

Product was isolated as a yellow foam (24% yield): ¹H NMR (CDCl₃) δ 7.63 (s, 1H), 7.29–7.39 (m, 3H), 7.21–7.24 (m, 2H), 7.11 (t, 1H), 4.03 (s, 3H), 2.21 (d, 3H); EI/MS 436 m/e (M⁺); Calcd. for $C_{20}H_{13}Cl_2F_2N_3S$: C, 55.1; H, 3.00; N, 9.63; Found: C, 55.0; H, 3.09; N, 9.47.

3-(2-Chloro-6-fluorophenyl)-5-[5-(2,4-difluorolphenyl)-4-methylthien-3-yl]-1-methyl-1H-1,2,4-triazole

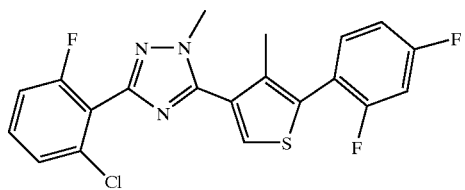

Product was isolated as a white solid (44% yield): mp 112–113° C.; ¹H NMR (CDCl₃) δ 7.62 (s, 1H), 7.29–7.39 (m, 3H), 7.11 (s, 1H), 6.92–7.00 (m, 2H), 4.04 (s, 3H), 2.21 (d, 3H); EI/MS 420 m/e (M⁺); Calcd. for $C_{20}H_{13}ClF_3N_3S$: C, 57.2; H, 3.12; N, 10.0; Found: C, 57.2; H, 3.21; N, 9.95.

3-(2-Chloro-6-fluorophenyl)-5-[5-(2-fluoro-3-trifluoromethylphenyl)-4-methylthien-3-yl]-1-methyl-1H-1,2,4-triazole

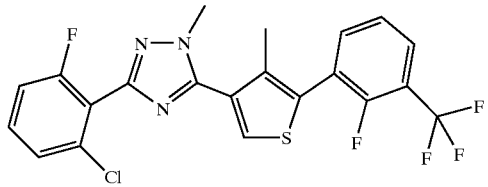

Product was isolated as a yellowish solid (54% yield): mp 127–128° C.; ¹H NMR (CDCl₃) δ 7.57–7.69 (m, 3H), 7.29–7.39 (m, 3H), 7.11 (t, 1H), 4.04 (s, 3H), 2.23 (d, 3H); EI/MS 470 m/e (M⁺).

3-(2-Chloro-6-fluorophenyl)-5-[5-(4-chloro-3-fluorophenyl)-4-methylthien-3-yl]-1-methyl-1H-1,24-triazole

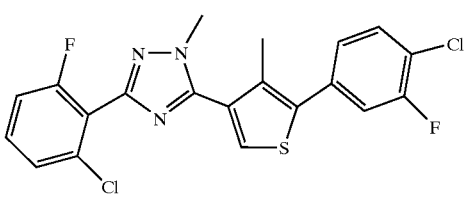

Product was isolated as a yellow solid (47% yield): mp 132° C.; ¹H NMR (CDCl₃) δ 7.56 (s, 1H), 7.47 (t, 1H), 7.27–7.37 (m, 2H), 7.19–7.25 (m, 2H), 7.11 (t, 1H), 4.03 (s, 3H), 2.33 (s, 3H); EI/MS 436 m/e (M⁺); Calcd. for $C_{20}H_{13}Cl_2F_2N_3S$: C, 55.1; H, 3.00; N, 9.63; Found: C, 55.3; H, 3.10; N, 9.47.

3-(2-Chloro-6-fluorophenyl)-5-[5-(2,3-dihydro-1,4-benzodioxin-6-yl)-4-methylthien-3-yl]-1-methyl-1H-1,2,4-triazole

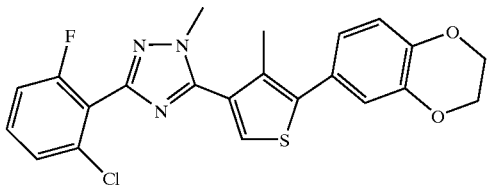

Product was isolated as a white solid (55% yield): mp 134–135° C.; ¹H NMR (CDCl₃) δ 7.47 (s, 1H), 7.28–7.38 (m, 2H), 7.10 (t, 1H), 6.99–6.96 (d, 1H), 6.94 (ds, 2H), 4.30 (s, 4H), 4.02 (s, 3H), 2.31 (s, 3H); EI/MS 442 m/e (M⁺); Calcd. for $C_{22}H_{17}ClFN_3O_2S$: C, 59.8; H, 3.88; N, 9.51; Found: C, 59.7; H, 4.06; N, 9.45.

3-(2-Chloro-6-fluorophenyl)-5-[5-(1,3-benzodioxin-5-yl)-4-methylthien-3-yl]-1-methyl-1H-1,2,4-triazole

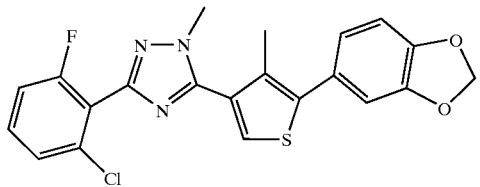

Product was isolated as white crystals (61% yield): mp 122–123° C.; $^1$H NMR (CDCl$_3$) δ 7.47 (s, 1H), 7.28–7.38 (m, 2H), 7.10 (d, 2H), 6.92–6.96 (m, 2H), 6.87 (d, 2H), 6.01 (d, 2H), 4.02 (s, 3H), 2.30 (s, 3H); EI/MS 428 m/e (M$^+$).

3-(2-Chloro-6-fluorophenyl)-5-{5-[4-(2-methoxyethoxy)phenyl]-4-methylthien-3-yl}-1-methyl-1H-1,2,4-triazole

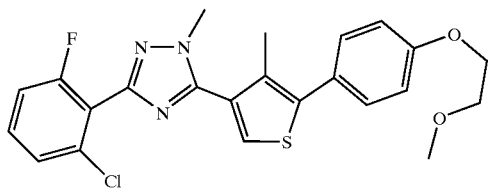

Product was isolated as a pale yellow glass (32% yield): $^1$H NMR (CDCl$_3$) δ 7.48 (s, 1H), 7.39 (d, 2H), 7.29–7.38 (m, 2H), 7.11 (t, 1H), 7.00 (d, 2H), 4.17 (m, 2H), 4.02 (s, 3H), 3.79 (m, 2H), 3.47 (s, 3H), 2.30 (s, 3H); EI/MS 457 m/e (M−1).

3-(2-Chloro-6-fluorophenyl)-5-{5-[4-(2-methylpropenyloxy)phenyl]-4-methylthien-3-yl}-1-methyl-1H-1,2,4-triazole

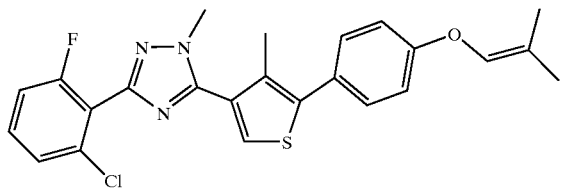

Product was isolated as a pale liquid (11% yield): $^1$H NMR (CDCl$_3$) δ 7.48 (s, 1H), 7.39 (d, 2H), 7.28–7.37 (m, 2H), 7.10 (t, 1H), 6.98 (d, 2H), 6.01–6.14 (m, 1H), 5.44 (d, 1H), 5.31 (d, 1H), 4.58 (d, 2H), 4.02 (s, 3H), 2.34 (s, 3H); EI/MS 439 m/e (M−CH$_3$).

3-(2-Chloro-6-fluorophenyl)-5-{5-[4-(1-methylethoxy)phenyl]-4-methylthien-3-yl]-1-methyl-1H-12.4-triazole

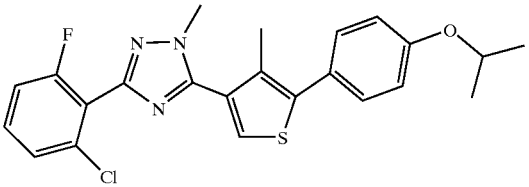

Product was isolated as a hard, yellowish glass (40% yield): $^1$H NMR (CDCl$_3$) δ 7.52 (s, 1H), 7.29–7.39 (m, 3H), 7.11 (t, 1H), 6.99–7.05 (m, 2H), 6.89 (d, 1H), 4.59 (pentet, 1H), 4.03 (s, 3H), 2.35 (s, 3H), 1.36 (d, 6H); EI/MS 441 m/e (M-1); Calcd. for C$_{23}$H$_{21}$ClFN$_3$OS: C, 62.5; H, 4.79; N, 9.51; Found: C, 62.7; H, 4.79; N, 9.50.

3-(2-Chloro-6-fluorophenyl)-5-[5-(2,4-dichlorophenyl)-4-methylthien-3-yl]-1-methyl-1H-1,2,4-triazole

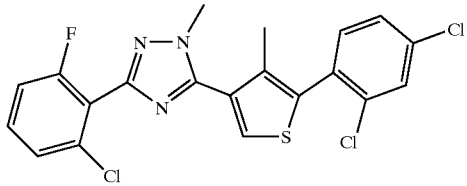

Product was isolated as white crystals (4% yield): mp 114–115° C.; $^1$H NMR (CDCl$_3$) δ 7.62 (s, 1H), 7.53 (s, 1H), 7.29–7.39 (m, 4H), 7.11 (t, 1H), 4.04 (s, 3H), 2.14 (s, 3H); EI/MS 453 m/e (M$^+$); Calcd. for C$_{20}$H$_{13}$Cl$_3$FN$_3$S: C, 53.1; H, 2.89; N, 9.28; Found: C, 52.9; H, 3.30; N, 8.86.

3-(2-Chloro-6-fluorophenyl)-5-[5-(3,4-dichlorophenyl)-4-methylthien-3-yl]-1-methyl-1H-1,2,4-triazole

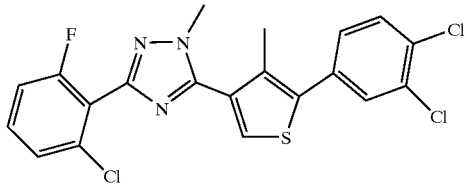

Product was isolated as a white solid (48% yield): mp 138° C.; $^1$H NMR (CDCl$_3$) δ 7.54 (d, 2H), 7.51 (s, 1H), 7.29–7.39 (m, 4H), 7.11 (t, 1H), 4.03 (s, 3H), 2.33 (s, 3H); EI/MS 452 m/e (M−1); Calcd. for C$_{20}$H$_{13}$Cl$_3$FN$_3$S: C, 53.1; H, 2.89; N, 9.28; Found: C, 53.1; H, 3.05; N, 9.24.

3-(2-chloro-6-fluorophenyl)-5-[3-methyl-5-(4-trifluoromethoxyphenyl)-thien-2-yl]-1-methyl-1H-1,2,4-triazole

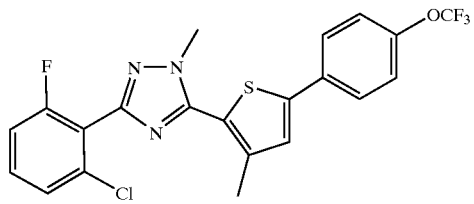

Product was isolated as a tan solid (72% yield): mp 96–97° C.; ¹H NMR (CDCl₃) δ 2.41 (s, 3H), 4.05 (s, 3H), 7.07 (m, 1H), 7.21–7.38 (m, 5H), 7.62 (d, 2H); EI/MS 467 m/e (M⁺).

3-(2-Chloro-6-fluorophenyl)-5-{3-methyl-5-[4-(trifluoromethyl)phenyl]-thien-2-yl}-1-methyl-1H-1,2,4-triazole

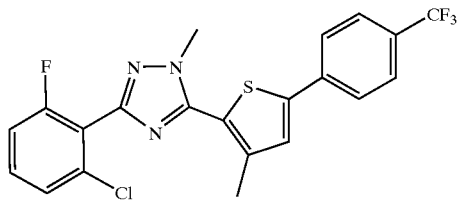

Product was isolated as an off-white solid (70% yield): mp 85–86° C.; ¹H NMR (CDCl₃) δ 2.43 (s, 3H), 4.12 (s, 3H), 7.10 (m, 1H), 7.25–7.41 (m, 3H), 7.72 (q, 4H, J=8.3 Hz); EI/MS 451 m/e (M⁺).

3-(2-Chloro-6-fluorophenyl)-5-[3-methyl-5-(3-chloro-4-fluorophenyl)-thien-2-yl]-1-methyl-1H-1,2,4-triazole

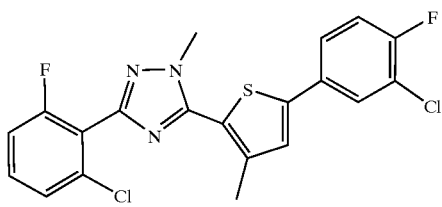

Product was isolated as a tan solid (58% yield): mp 121–122° C.; ¹H NMR (CDCl₃) δ 2.25 (s, 3H), 3.95 (s, 3H), 6.95–7.22 (m, 5H), 7.31 (m, 1H), 7.55 (d, 2H); EI/MS 436 m/e (M⁺).

3-(2,6-difluorophenyl)-5-{3-chloro-5-[4-(trifluoromethoxy)phenyl]thien-2-yl}-1-methyl-1H-1,2,4-triazole

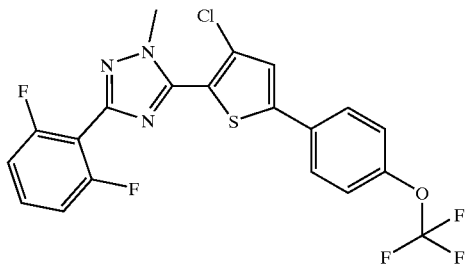

Product was isolated as a yellow solid (65% yield): mp 105–107° C.; ¹H NMR (CDCl₃) δ 7.63–7.59 (m, 2H), 7.41–7.36 (m, 1H), 7.30–7.25 (m, 3H), 7.06–7.00 (m, 2H), 4.07 (s, 3H); EI/MS 471 m/e (M⁺); Calcd for $C_{20}H_{11}ClF_5N_3OS$: C, 50.91; H, 2.35; N, 8.91; S, 6.80; Found: C, 50.90; H, 2.44; N, 8.64; S, 6.93.

3-(2,6-Difluorophenyl)-5-[3-chloro-5-(4-methylphenyl)thien-2-yl]-1-methyl-1H-1,2,4-triazole

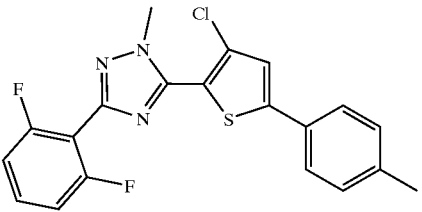

Product was isolated as an off-white foamy solid (69% yield): mp 139–141° C.; ¹H NMR (CDCl₃) δ 7.47 (m, 2H), 7.41–7.35 (m, 1H), 7.26–7.22 (m, 3H), 7.05–7.02 (m, 2H), 4.07 (s, 3H), 2.39 (s, 3H); EI/MS 401 m/e (M⁺); Calcd for $C_{20}H_{14}ClF_2N_3S$: C, 59.78; H, 3.51; N, 10.46; S, 7.98; Found: C, 59.83; H, 3.61; N, 10.22; S, 8.16.

3-(2,6-Difluorophenyl)-5-[3-chloro-5-(4-ethoxyphenyl)thien-2-yl]-1-methyl-1H-1,2,4-triazole

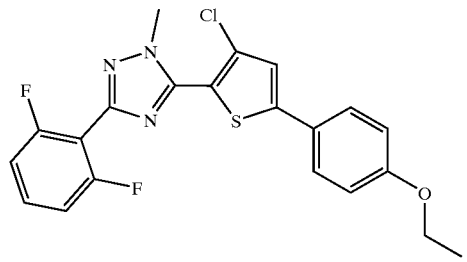

Product was isolated as a light yellow solid (64% yield): mp 120–123° C.; ¹H NMR (CDCl₃) δ 7.50 (d, 2H, J=8.7 Hz), 7.38 (m, 1H), 7.15 (s, 1H), 7.05–6.99 (m, 2H), 6.94 (d, 2H, J=8.7 Hz), 4.06 (m, 5H), 1.44 (t, 3H, J=6.9 Hz); EI/MS 432 m/e (M+H); Calcd for $C_{21}H_{16}ClF_2N_3OS$: C, 58.40; H, 3.73; N, 9.73; S, 7.42; Found: C, 58.44; H, 3.88; N, 9.48; S, 7.23.

3-(2,6-Difluorophenyl)-5-{3-chloro-5-[4-trifluoromethyl)phenyl]thien-2-yl}-1-methyl-1H-1¹2,4-triazole

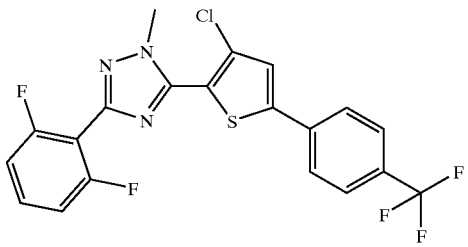

Product was isolated as a white solid (63% yield): mp 156–162° C.; ¹H NMR (CDCl₃) δ 7.70 (s, 4H), 7.42–7.35 (m, 2H), 7.03 (t, 2H, J=8.05 Hz), 4.08 (s, 3H); EI/MS 455 m/e (M⁺); Calcd for $C_{20}H_{11}ClF_5N_3S$: C, 52.70; H, 2.43; N, 9.22; S, 7.03; Found: C, 52.81; H, 2.50; N, 9.13; S, 7.11.

3-(2-Chloro-6-fluorophenyl)-5-{3-chloro-5-[4-trifluoromethoxy)phenylthien-2-yl}-1-methyl-1H-1,2,4-triazole

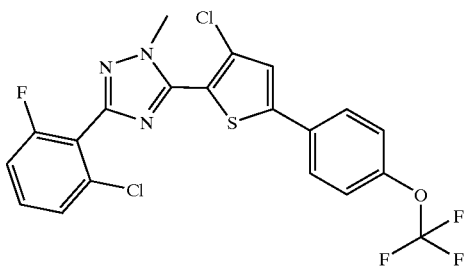

Product was isolated as an off-white solid (62% yield): mp 120–123° C.; ¹H NMR (CDCl₃) δ 7.62 (ddd, 2H, J=2.1, 2.9, 8.7 Hz), 7.40–7.26 (m, 5H), 7.15–7.08 (m, 1H), 4.08 (s, 3H); EI/MS 487 m/e (M⁺); Calcd for $C_{20}H_{11}Cl_2F_4N_3OS$: C, 49.20; H, 2.27; N, 8.61; S, 6.57; Found: C, 49.42; H, 2.38; N, 8.37; S, 6.61.

3-(2-Chloro-6-fluorophenyl)-5-{3-chloro-5-[4-(trifluoromethyl)phenyl]thien-2-yl}-1-methyl-1H-1,2,4-triazole

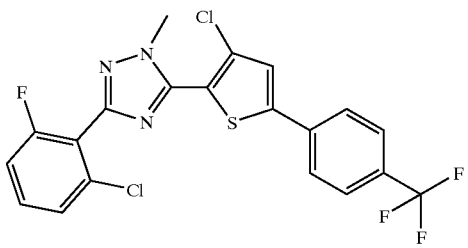

Product was isolated as an off-white solid (60% yield): mp 133–136° C.; ¹H NMR (CDCl₃) δ 7.70 (s, 4H), 7.38–7.30 (m, 3H), 7.15–7.09 (m, 1H), 4.09 (s, 3H); EI/MS 471 m/e (M⁺); Calcd for $C_{20}H_{11}Cl_2F_4N_3S$: C, 50.86; H, 2.35; N, 8.90; S, 6.79; Found: C, 51.01; H, 2.36; N, 8.67; S, 6.48.

3-(2-Chloro-6-fluorophenyl)-5-[3-chloro-5-(4-methylphenyl)thien-2-yl]-1-methyl-1H-1,2,4-triazole

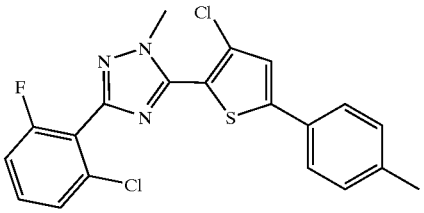

Product was isolated as a light yellow solid (69% yield): mp 111–115° C.; ¹H NMR (MHz, CDCl₃) δ 7.49 (d, 2H, J=8.0 Hz), 7.46–7.23 (m, 5H), 7.14–7.08 (m, 1H), 4.09 (s, 3H); EI/MS 417 m/e (M⁺); Calcd for $C_{20}H_{14}Cl_2FN_3S$: C, 57.43; H, 3.37; N, 10.04; S, 7.66; Found: C, 57.19; H, 3.46; N, 9.64; S, 7.16.

3-(2-Chloro-6-fluorophenyl)-5-[3-chloro-5-(4-ethoxyphenyl)thien-2-yl]-1-methyl-1H-1,2,4-triazole

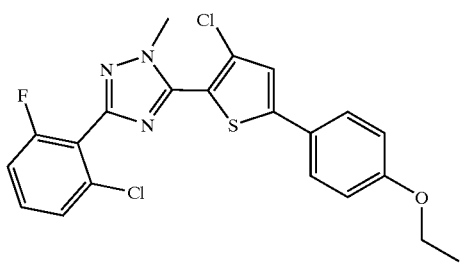

Product was isolated as an off-white solid (66% yield): mp 126–128° C.; ¹H NMR (CDCl₃) δ 7.50 (dd, 2H, J=8.7, 2.0 Hz), 7.39–7.29 (m, 2H), 7.15 (s, 1H), 7.14–7.08 (m, 1H), 6.96–6.92 (m, 1H), 4.11 (m, 5H), 1.44 (t, 3H, J=7.1 Hz); EI/MS 419 m/e (M-Et); Calcd for $C_{21}H_{16}Cl_2FN_3OS$: C, 56.26; H, 3.60; N, 9.37; S, 7.15; Found: C, 56.33; H, 3.62; N, 9.31; S, 7.13.

3-(2-Chloro-6-fluorophenyl)-5-[5-(4-bromophenyl)-3-chlorothien-2-yl]-1-methyl-1H-1,2,4-triazole

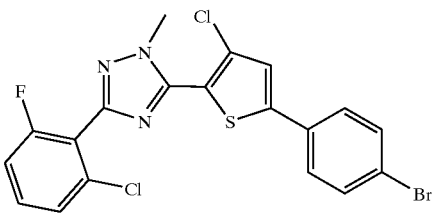

Product was isolated as an off-white solid (44% yield): mp 126–128° C.; ¹H NMR (CDCl₃) δ 7.57 (d, 2H, J=8.4 Hz), 7.46 (d, 2H, J=8.4 Hz), 7.37–7.29 (m, 2H), 7.26 (s, 1H and CDCl₃), 7.14–7.08 (m, 1H), 4.08 (s, 3H); EI/MS 483 m/e (M⁺); Calcd for $C_{19}H_{11}BrCl_2FN_3S$: C, 47.23; H, 2.29; N, 8.70; S, 6.64; Found: C, 47.32; H, 2.34; N, 8.46; S, 6.68.

3-(2-Chloro-6-fluorophenyl)-5-{3-chloro-5-[4-(methylthio)phenyl]thien-2-yl}-1-methyl-1H-1,2,4-triazole

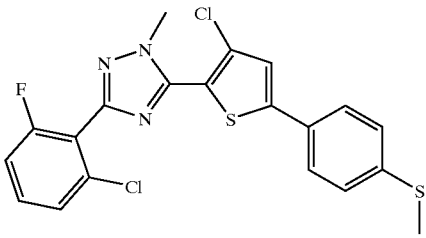

Product was isolated as a light yellow solid (66% yield): mp 125–126° C.; $^1$H NMR (CDCl$_3$) δ 7.50 (d, 2H, J=8.7 Hz), 7.40–7.23 (m, 5H), 7.14–7.08 (m, 1H), 4.08 (s, 3H), 2.52 (s, 3H); EI/MS 449 m/e (M$^+$); Calcd for C$_{20}$H$_{14}$Cl$_2$FN$_3$S$_2$: C, 53.34; H, 3.13; N, 9.33; S, 14.24; Found: C, 53.17; H, 3.19; N, 9.19; S, 14.28.

3-(2-Chloro-6-fluorophenyl)-5-{4-bromo-3-chloro-5-[4-(trifluoromethoxy)-phenyl]thien-2-yl}-1-methyl-1H-1,2,4-triazole

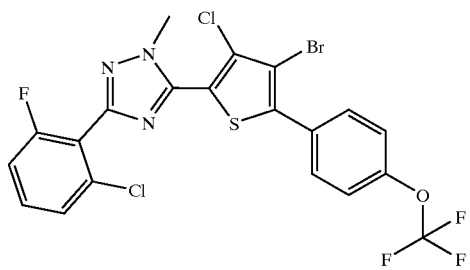

Product was isolated as a white solid (18%): mp 170–172° C.; $^1$H NMR (CDCl$_3$) δ 7.69 (d, 2H, J=8.7 Hz), 7.38–7.29 (m, 4H), 7.23–7.09 (m, 1H), 4.09 (s, 3H); EI/MS 567 m/e (M$^+$).

3-(2-Chloro-6-fluorophenyl)-5-{4-bromo-3-chloro-5-[4-(trifluoromethyl)phenyl]-thien-2-yl}-1-methyl-1H-1,2,4-triazole

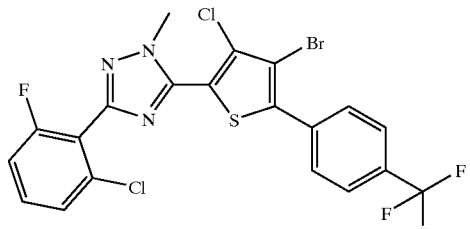

Product was isolated as a white solid (28% yield): mp 167–170° C.; $^1$H NMR (CDCl$_3$) δ 7.50 (dd, 2H, J=8.7, 2.0 Hz), 7.39–7.29 (m, 2H), 7.15 (s, 1H), 7.14–7.08 (m, 1H), 6.96–6.92 (m, 1H), 4.11 (m, 5H), 1.44 (t, 3H, J=7.1 Hz); EI/MS 551 m/e (M$^+$).

3-(2-Chloro-6-fluorophenyl)-5-[4-bromo-3-chloro-5-(4-ethoxyphenyl)thien-2-yl]-1-methyl-1H-1,2,4-triazole

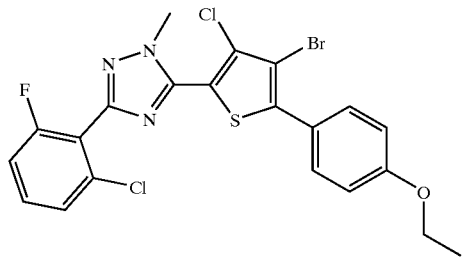

Product was isolated as a white solid (41% yield): mp 145–150° C.; $^1$H NMR (CDCl$_3$) δ 7.58 (d, 2H, J=8.7 Hz), 7.40–7.30 (m, 2H), 7.14–7.08 (m, 1H), 6.99 (d, 2H, J=8.7 Hz), 4.13–4.03 (m, 5H), 1.45 (t, 3H, J=6.9 Hz); EI/MS m/e 527 (M$^+$).

3-(2-Chloro-6-fluorophenyl)-5-[4-(4-trifluoromethoxyphenyl)-3-methylthien-2-yl]-1-methyl-H-1,2,4-triazole

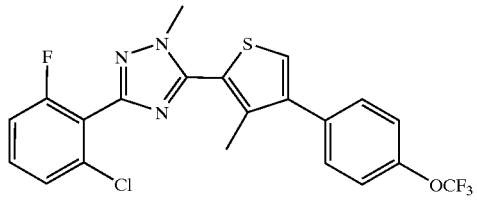

Product was isolated as an off-white solid (69% yield): mp 108–109° C.; $^1$H NMR (CDCl$_3$) δ 2.16 (s, 3H), 3.92 (s, 3H), 6.96 (m, 1H), 7.11–7.29 (m, 7H); EI/MS 467 m/e (M$^+$)

3-(2-Chloro-6-fluorophenyl)-5-[4-(4-ethoxyphenyl)-3-methylthien-2-yl]-1-methyl-1H-1,2,4-triazole

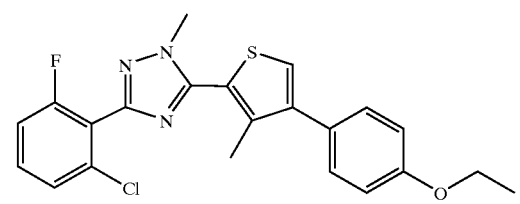

Product was isolated as an off-white solid (80% yield): mp 124–127° C.; $^1$H NMR (CDCl$_3$) δ 1.45 (t, 3H, J=7.0 Hz), 2.31 (s, 3H), 4.06 (s, 3H), 6.96 (d, 2H, J=8.4 Hz), 6.98–7.13 (m, 1H), 7.30–7.39 (m, 5H); EI/MS 427 m/e (M+H); Calcd. for C$_{22}$H$_{19}$ClFN$_3$OS: C, 61.75; H, 4.48; N, 9.82; Found: C, 61.74; H, 4.53; N, 9.63.

3-(2-Chloro-6-fluorophenyl)-5-[4-(4-trifluoromethylphenyl)-3-methylthien-2-yl]-1-methyl-1H-1,2,4-triazole

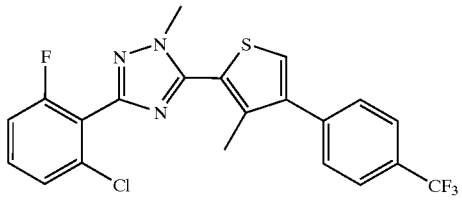

Product was isolated as a white solid (66% yield): mp 102–103° C.; $^1$H NMR (CDCl$_3$) δ 2.34 (s, 3H), 4.08 (s, 3H), 7.10 (dd, 1H, J=7.3 Hz), 7.31–7.38 (m, 2H), 7.49 (s, 1H), 7.53 (d, 2H, J=8.0 Hz), 7.71 (d, 2H, J=8.0 Hz); EI/MS 467 m/e (M$^+$).

3-(2-Chloro-6-fluorophenyl)-5-F4-(4-isopropylphenyl)-3-methylthien-2-yl]-1-methyl-1H-1,2,4-triazole

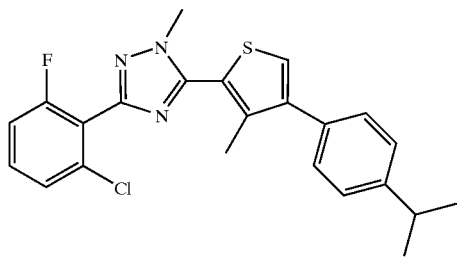

Product was isolated as a white solid (53% yield): mp 109–111° C.; $^1$H NMR (CDCl$_3$) δ 1.30 (d, 6H, J=6.6 Hz), 2.33 (s, 3H), 2.96 (m, 1H), 4.06 (s, 3H), 7.08–7.14 (m, 1H), 7.28–7.38 (m, 7H); EI/MS 425 m/e (M+H); Calcd. for C$_{23}$H$_{23}$ClFN$_3$S: C, 64.86; H, 4.97; N, 9.86; Found: C, 64.51; H, 5.02; N, 9.78.

3-(2-Methylphenyl)-5-{4-methyl-5-[4-trifluoromethoxyphenyl]thien-3-yl}-1-methyl-1H-1,2,4-triazole

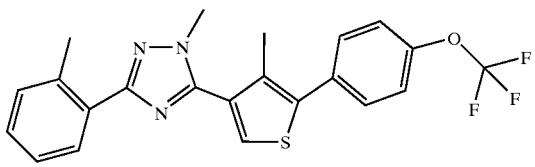

Product was obtained as a yellowish solid (83% yield): mp 122–123° C.; $^1$H NMR (CDCl$_3$) δ 7.98–8.01 (m, 1H), 7.48–7.52 (m, 3H), 7.27–7.32 (m, 5H), 3.98 (s, 3H), 2.69 (s, 3H), 2.33 (s, 3H); EI/MS 430 m/e (M+1).

3-(2-Methylphenyl)-5-{4-methyl-5-[4-trifluoromethylphenyl]thien-3-yl}-1-methyl-1H-1,2,4-triazole

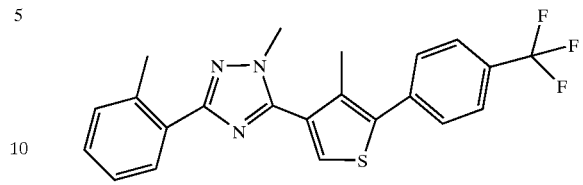

Product was obtained as a yellow solid (68% yield): mp 149–150° C.; $^1$H NMR (CDCl$_3$) δ 7.98–8.00 (m, 1H), 7.71 (d, J=8.1 Hz, 2H), 7.61 (d, J=8.4 Hz, 2H), 7.56 (s, 1H), 7.27–7.30 (m, 3H), 3.99 (s, 3H), 2.69 (s, 3H), 2.36 (s, 3H); EI/MS 414 m/e (M+1).

3-(2-Methylphenyl)-5-[5-(4-ethoxyphenyl)-4-methylthien-3-yl]-1-methyl-1H-1,2,4-triazole

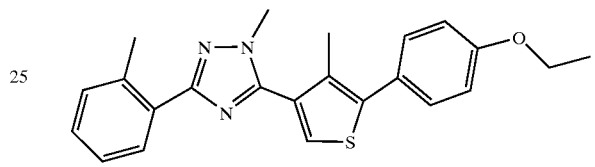

Product was obtained as white needles (11% yield): mp 160–161° C.; $^1$H NMR (CDCl$_3$) δ 7.98–8.01 (m, 1H), 7.44 (s, 1H), 7.29–7.43 (m, 2H), 7.26–7.29 (m, 3H), 6.94–6.99 (m, 2H), 4.08 (q, J=6.9 Hz, 2H), 3.98 (s, 3H), 2.69 (s, 3H), 2.31 (s, 3H), 1.45 (t, J=7.2 Hz, 3H); EI/MS 390 m/e (M+1).

Example 2

3-(2-Chloro-6-fluorophenyl)-5-[2-chloro-5-(3-trifluoromethylphenyl)thien-3-yl]-1-methyl-1H-12,4-triazole

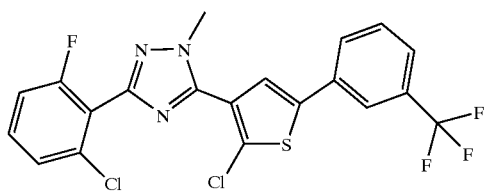

A solution of 3-(2-chloro-6-fluorophenyl)-1-methyl-5-[5-(3-trifluoromethylphenyl)thien-3-yl]-1H-1,2,4-triazole (0.45 g, 1 mmol) and N-chlorosuccinimide (0.15 g, 1.1 mmol) in methylene chloride/glacial acetic acid (1:1, 2 mL) was refluxed under nitrogen for 2 days, cooled to room temperature, poured into water (10 mL) and extracted with ether (3×20 mL). The combined ethereal extracts were washed with water (3×30 mL), saturated aqueous sodium bicarbonate (50 mL) and brine (30 mL), dried over magnesium sulphate and chromatographed on silica to afford the product as a white solid (0.37 g, 76%): mp 53–54° C.; $^1$H NMR (CDCl$_3$) δ 7.79 (s, 1H), 7.71 (d, 2H), 7.60 (d, 1H), 7.54 (t, 1H), 7.44 (s, 1H), 7.307.40 (m, 2H), 7.11 (t, 1H), 4.05 (s, 3H); EI/MS 472 m/e (M$^+$); Calcd. for C$_{20}$H$_{11}$Cl$_2$F$_4$N$_3$S: C, 50.9; H, 2.35; N, 8.90; Found: C, 50.9; H, 2.49; N, 8.82.

The following compounds were prepared according to the general procedure of Example 2.

3-(2-Chloro-6-fluorophenyl)-5-[2-chloro-5-(3-trifluoromethoxyphenyl)thien-3-yl]-1-methyl-1H-1,2,4-triazole

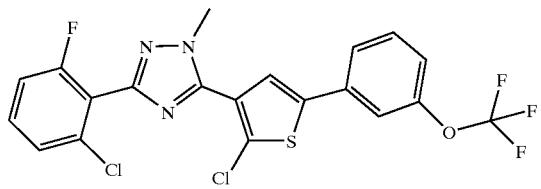

Product was isolated as a white solid (96% yield): mp 98–99° C.; $^1$H NMR (CDCl$_3$) δ 7.29–7.46 (m, 6H), 7.21 (br, 1H), 7.11 (t, 1H), 4.04 (s, 3H); EI/MS 488 m/e (M$^+$); Calcd. for C$_{20}$H$_{11}$Cl$_2$F$_4$N$_3$OS: C, 49.2; H, 2.27; N, 8.61; Found: C, 49.4; H, 2.40; N, 8.49.

3-(2-Chloro-6-fluorophenyl)-5-[2-chloro-5-(2-fluoro-4-trifluoromethylphenyl)-thien-3-yl]-1-methyl-1H-1,2,4-triazole

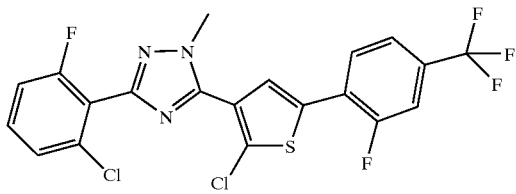

Product was isolated as a white solid (66% yield): mp 157–158° C.; $^1$H NMR (CDCl$_3$) δ 7.72 (t, 1H), 7.62 (s, 1H), 7.44–7.49 (m, 2H), 7.33–7.38 (m, 2H), 7.12 (t, 1H), 4.04 (s, 3H); EI/MS 490 m/e (M$^+$); Calcd. for C$_{20}$H$_{10}$Cl$_2$F$_5$N$_3$S: C, 49.0; H, 2.06; N, 8.57; Found: C, 48.5; H, 2.29; N, 8.34.

3-(2-Chloro-6-fluorophenyl)-5-[2-chloro-5-(4-chloro-2-fluorophenyl)thien-3-yl]-1-methyl-1H-1,2,4-triazole

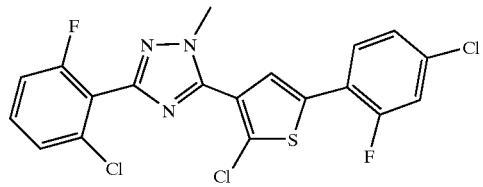

Product was isolated as white, iridescent flakes (57% yield): mp 197–198° C.; $^1$H NMR (CDCl$_3$) δ 7.49–7.54 (m, 2H), 7.29–7.38 (m, 2H), 7.18–7.24 (m, 2H), 7.11 (t, 1H), 4.04 (s, 3H); EI/MS 458 m/e (M+1); Calcd. for C$_{19}$H$_{10}$Cl$_3$F$_2$N$_3$S; C, 50.0; H, 2.21; N, 9.20; Found: C, 49.6; H, 2.31; N, 8.94.

3-(2-Chloro-6-fluorophenyl)-5-[2-chloro-5-(4-trifluoromethylphenyl)thien-3-yl]-1-methyl-1H-1,2,4-triazole

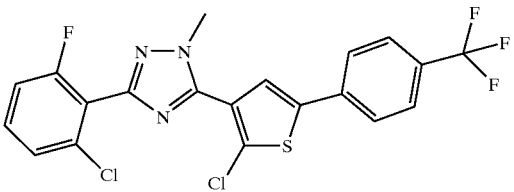

Product was isolated as an amorphous white solid (64% yield): mp 145–146° C.; $^1$H NMR (CDCl$_3$) δ 7.66 (dd, 4H), 7.46 (s, 1H), 7.30–7.40 (m, 2H), 7.12 (m, 1H), 4.05 (s, 3H); EI/MS 472 m/e (M$^+$).

3-(2-Chloro-6-fluorophenyl)-5-[2-chloro-5-(4-trifluoromethoxyphenyl)thien-3-yl]-1-methyl-1H-1,2,4-triazole

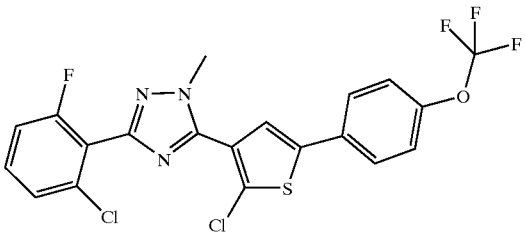

Product was isolated as needles (12% yield): mp 154–155° C.; $^1$H NMR (CDCl$_3$) δ 7.56 (d, 2H), 7.30–7.40 (m, 2H), 7.25–7.28 (m, 3H), 7.11 (m, 1H), 4.04 (s, 3H); EI/MS 488 m/e (M$^+$).

Example 3

3-(2-Chloro-6-fluorophenyl)-5-[2-bromo-5-(4-trifluoromethoxyphenyl)thien-3-yl]-1-methyl-1H-1,2,4-triazole

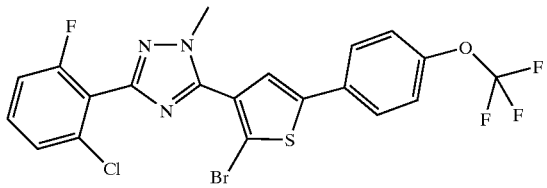

A solution of 3-(2-chloro-6-fluorophenyl)-1-methyl-5-[5-(4-trifluoromethoxyphenyl)thien-3-yl]-1H-1,2,4-triazole (0.26 g, 0.6 mmol) in glacial acetic acid (7 mL) was cooled to 6° C. Bromine (0.1 g, 32 μL, 0.6 mmol) was added to the reaction and allowed to warm to room temperature and stirred for 16 hours. The reaction mixture was poured into water (50 mL) and extracted with ether (3×30 mL). The combined ethereal extracts were washed with water (100 mL), saturated aqueous sodium bicarbonate (100 mL), aqueous sodium bisulphite (10% solution, 50 mL) and brine (70 mL), dried over magnesium sulphate and concentrated. Column chromatography gave the product (297 mg, 97%) as a yellowish solid: mp 135–136° C.; $^1$H NMR (CDCl$_3$) δ 7.57 (d, 1H), 7.25–7.40 (m, 5H), 7.12 (t, 1H), 4.04 (s, 3H); EI/MS 533 m/e (M$^+$).

The following compounds were prepared according to the general procedure of Example 3.

3-(2-Chloro-6-fluorophenyl)-5-[2-bromo-4-methyl-5-(4-trifluoromethoxyphenyl)-thien-3-yl]-1-methyl-1H-1,2,4-triazole

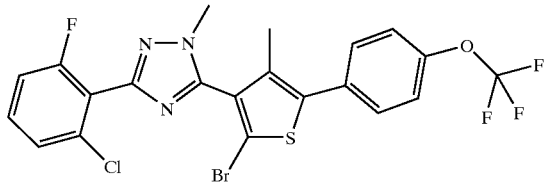

Product was isolated as a clear, thick gum (99% yield): IR NMR (CDCl₃) δ 7.42 (d, 2H), 7.27–7.31 (m, 4H), 7.10 (t, 1H), 3.97 (s, 3H), 2.18 (s, 3H); EI/MS 547 m/e (M⁺).

Example 4

3-(2-Chloro-6-fluorophenyl)-5-[2-methyl-5-(4-trifluoromethoxyphenyl)thien-3-yl]-1-methyl-1H-1,2,4-triazole

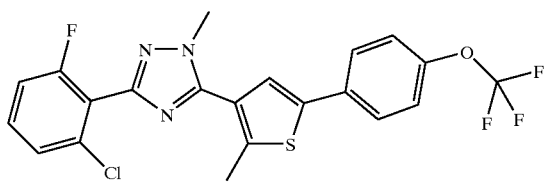

n-Butyllithium (2.5 N in hexanes, 0.25 mL, 0.4 mmol) was added to a solution of 3-(2-chloro-6-fluorophenyl)-5-[2-bromo-5-(4-trifluoromethoxyphenyl)thien-3-yl]-1-methyl-1H-1,2,4-triazole (190 mg, 0.3 mmol) in dry THF (2 mL) at −75° C. and stirred for 1 hour. Iodomethane (66 mg, 29 μL, 0.5 mmol) was added to this reaction mixture and stirred at −75° C. for 30 minutes. After warming to 0° C., saturated aqueous ammonium chloride (2 mL) was added, followed by water (30 mL) and the mixture was extracted with ether (3×10 mL). The combined ethereal extracts were washed with water (30 mL) and brine (10 mL), dried over magnesium sulphate and chromatographed on silica to give the product (49 mg, 29%) as a yellow solid: mp 153–155° C.; ¹H NMR (CDCl₃) δ 7.59 (d, 2H), 7.29–7.39 (m, 3H), 7.25 (d, 2H), 7.12 (t, 1H), 4.01 (s, 3H), 2.62 (s, 3H); EI/MS 467 m/e (M−1).

The following compounds were prepared according to the general procedure of Example 4.

3-(2-Chloro-6-fluorophenyl)-5-[2,4-dimethyl-5-(4-trifluoromethoxyphenyl)thien-3-yl]-1-methyl-1H-1,24-triazole

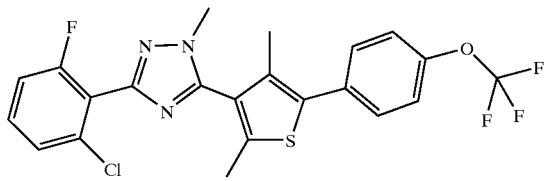

Product was isolated as a hard, colourless glass (59% yield): ¹H NMR (CDCl₃) δ 7.45–7.47 (d, 2H), 7.28–7.40 (m, 4H), 7.12 (t, 1H), 3.98 (s, 3H), 2.41 (s, 3H), 2.13 (s, 3H); EI/MS 481 m/e (M−1).

3-(2-Chloro-6-fluorophenyl)-5-[2-chloro-4-methyl-5-(4-trifluoromethoxyphenyl)-thien-3-yl]-1-methyl-1H-1,2,4-triazole

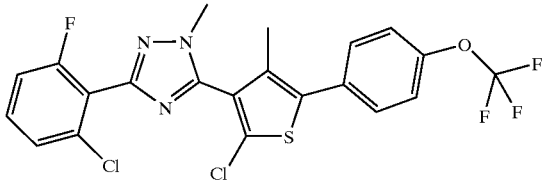

Product was isolated as a colourless gum (65% yield): ¹H NMR (CDCl₃) δ 7.45 (d, 2H), 7.28–7.38 (m, 4H), 7.12 (t, 1H), 3.98 (s, 3H), 2.18 (s, 3H); EI/MS 501 m/e (M−1).

Example 5

3-(2-Chloro-6-fluorophenyl)-5-[(5-(4-fluoromethylthio)phenyl)-4-methylthien-3-yl]-1-methyl-1H-1,2,4-triazole

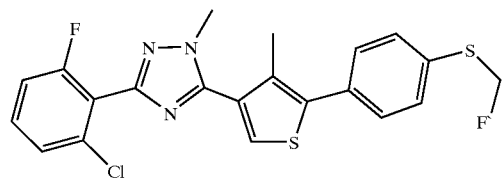

A solution of 3-(2-chloro-6-fluorophenyl)-5-[4-methyl-5-(4-methlsulfinyl phenyl)-thien-3-yl]-1-methyl-1H-1,2,4-triazole (160 mg, 0.36 mmol) in chloroform (4 mL) was treated with (diethylamino)sulphur trifluoride (77 mg, 0.5 mmol) and antimony trifluoride (1.1 mg, 4.8 nmol). Suspended solids gradually dissolved upon stirring at room temperature. Saturated aqueous sodium bicarbonate (3 mL) and 50% aqueous sodium hydroxide (1 drop via Pasteur pipette) were added after 5 hours stirring at room temperature. The organic phase was collected and the aqueous phase was extracted with chloroform (2×10 mL). The combined organic extracts were washed with water (10 mL), saturated sodium bicarbonate (10 mL) and brine (10 mL), dried over magnesium sulphate and chromatographed on silica gel to furnish the target compound (22 mg, 37%): ¹H NMR (CDCl₃) δ 7.55–7.58 (m, 3H), 7.46 (d, 2H), 7.29–7.39 (m, 2H), 7.11 (t, 1H), 5.86 (s, 1H), 5.69 (s, 1H), 4.03 (s, 3H), 2.34 (s, 3H); EI/MS 447 m/e (M+1).

Example K

4-{4-Chloro-5-[3-(2-chloro-6-fluorophenyl)-1-methyl-1H-1,2,4-triazol-5-yl]thien-2-yl}phenol

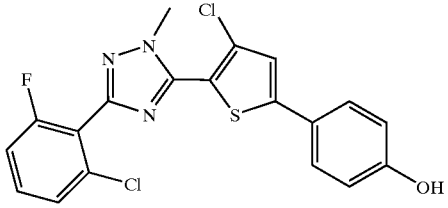

5-[3-Chloro-5-(4-ethoxyphenyl)thien-2-yl]-3-(2-chloro-6-fluorophenyl)-1-methyl-1H-1,2,4-triazole (542 mg, 1.20 mmol) was dissolved in $CH_2Cl_2$ (12 mL) under $N_2$ and was cooled to 0° C. To this was added $BBr_3$ (1.0 M solution in $CH_2Cl_2$; 2.0 mL, 2.0 mmol) dropwise via syringe. The cooling bath was removed immediately and the reaction mixture was allowed to warm to 25° C. and stirred for 20 hours. The mixture was poured onto $H_2O$ (100 mL) and stirred at 25° C. for 30 min. The layers were partitioned, and the aqueous layer was extracted with $CH_2Cl_2$ (2×50 mL). The combined organic extracts were washed with $H_2O$ (50 mL) and satd aq NaCl (50 mL), dried ($Na_2SO_4$), filtered and concentrated. Column chromatography (10–80% $Et_2O$-hexanes) gave the product (414 mg, 81%) as a light yellow solid: mp 205–209° C.; $^1H$ NMR ($CDCl_3$) δ 7.38 (m, 2H), 7.34–7.25 (m, 2H), 7.09–7.03 (m, 2H), 6.80 (m, 2H), 4.00 (s, 3H); EI/MS 420 m/e (M+).

The following compounds were prepared according to the general procedure of Example K.

3-(2-Chloro-6-fluorophenyl)-5-[5-(4-hydroxyphenyl)-4-methylthien-3-yl]-1-methyl-1H-1,2,4-triazole

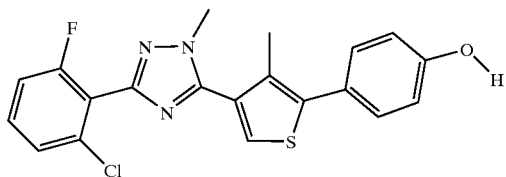

Product was isolated as white plates (42% yield): mp 221–222° C.; $^1H$ NMR ($CDCl_3$) δ 7.47 (s, 1H), 7.26–7.37 (m, 4H), 7.11 (t, 1H), 6.84 (d, 2H), 5.77 (br, 1H), 4.02 (s, 3H), 2.25 (s, 3H); EI/MS 399 m/e (M–1).

4-=3-Chloro-4-[3-(2-chloro-6-fluorophenyl)-1-methyl-1H-1,2,4-triazol-5-yl]thien-2-yl}phenol

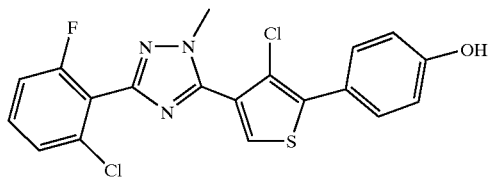

Product was isolated as a salmon-colored solid (27% yield): mp 239–242° C.; $^1H$ NMR ($CDCl_3$) δ 7.59 (s, 1H), 7.49 (d, 2H, J=8.05 Hz), 7.35–7.28 (m, 2H), 7.15–7.10 (m, 1H), 6.85 (d, 2H, J=8.42), 6.31 (bs, 1H), 4.00 (s, 3H); EI/MS 420 m/e (M+H), 418 m/e (M–H).

4-{5-[3-(2-Chloro-6-fluorophenyl)-1-methyl-1H-1,2,4-triazol-5-yl]-4-methylthien-3-yl}phenol

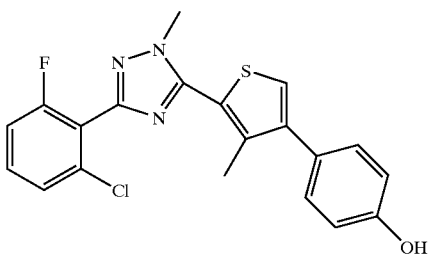

Product was isolated as an off-white solid (50% yield): mp 233–235° C.; $^1H$ NMR ($CDCl_3$) δ 2.29 (s, 3H), 4.06 (s, 3H), 5.03 (s, 1H), 6.88 (d, 2H, J=8.4 Hz), 7.08–7.13 (m, 1H), 7.24–7.27 (m, 3H), 7.30–7.36 (m, 2H); EI/MS 399 ni/e (M–H); Calcd. for $C_{20}H_{15}ClFN_3OS$: C, 60.07; H, 3.78; N, 10.51; Found: C, 60.06; H, 3.88; N, 10.28.

Example L 3-(2-Chloro-6-fluorophenyl)-5-[5-(4-hydroxyphenyl)-4-methylthien-3-yl]-1-methyl-1H-1,2,4-triazole

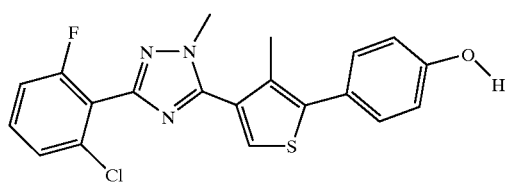

Dilute hydrochloric acid (4 N, 2.5 mL) was added to a suspension of 3-(2-chloro-6-fluorophenyl)-5-{4-methyl-5-[4-(tetrahydro-2H-pyran-2-yloxy)phenyl]thien-3-yl}-1-methyl-1H-1,2,4-triazole (0.62 g, 1.3 mmol) in tetrahydrofuran (2.5 mL), stirred at room temperature for 30 minutes, poured into water (20 mL) and extracted with ether (3×20 mL). The combined ethereal extracts were washed with water (100 mL) and brine (50 mL), dried over magnesium sulphate and concentrated under reduced pressure to leave the desired product (0.49 g, 96%) as a white solid. $^1H$ NMR ($CDCl_3$) and mass spectrometry data indicated this material to be free of impurities and to be comparable to authentic material prepared according to that in Example K.

Example 6

3-(2-Chloro-6-fluorophenyl)-5-[4-methyl-5-(4-n-propoxyphenyl)thien-3-yl]-1-methyl-1H-1,2,4-triazole

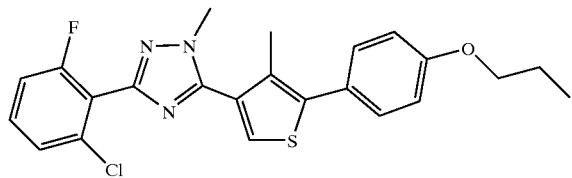

A solution of 3-(2-chloro-6-fluorophenyl)-5-[5-(4-hydroxyphenyl)-4-methylthien-3-yl]-1-methyl-1H-1,2,4-triazole (97 mg, 0.2 mmol) in dry THF (2 mL) was cooled to −3° C. and treated with sodium hydride (95% suspension in mineral oil, 9 mg, 0.4 mmol). After stirring for 5 minutes, iodopropane (62 mg, 0.4 mmol) was added and the reaction was allowed to stir at room temperature for 16 hours. An additional batch of sodium hydride (9 mg, 0.4 mmol) and iodopropane (62 mg, 0.4 mmol) was added and the reaction heated to 45° C. After dilution with water (5 mL), the product was extracted with ether (3×5 mL). The combined ethereal extracts were washed with water (2×5 mL) and brine (10 mL), dried over magnesium sulphate and concentrated. Column chromatography gave the product (101 mg, 93%) as a colorless glass: $^1$H NMR (CDCl$_3$) δ 7.49 (s, 1H), 7.27–7.41 (m, 4H), 7.12 (t, 1H), 6.98 (d, 2H), 4.04 (s, 3H), 3.99 (t, 2H), 2.32 (s, 3H), 1.85 (m, 2H), 1.08 (t, 3H); EI/MS 441 m/e (M+1).

The following compounds were prepared according to the general procedure of Example 6.

3-(2-Chloro-6-fluorophhenyl)-5-{4-methyl-5-[4-(2,2,2-trifluoroethoxy)phenyl]-thien-3-yl}-1-methyl-1H-1,2,4-triazole

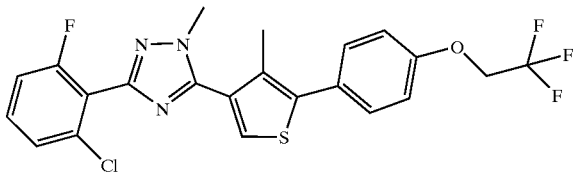

Product was isolated as white plates (15% yield): mp 161–162° C.; $^1$H NMR (CDCl$_3$) δ 7.62 (s, 1H), 7.57 (d, 2H), 7.32–7.39 (m, 2H), 7.11 (t, 1H), 7.03 (d, 2H), 4.42 (q, 2H), 4.03 (s, 3H), 2.31 (s, 3H); EI/MS 481 m/e (M+1).

3-(2-Chloro-6-fluorophenyl)-5–15-[4-(2-fluoroethoxy)phenyl]-4-methylthien-3-yl 1–1-methyl-1H-1,2,4-triazole

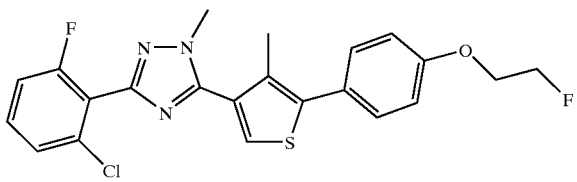

Product was isolated as colourless cubes (43% yield): mp 121–122° C.; $^1$H NMR (CDCl$_3$) δ 7.49 (s, 1H), 7.41 (d, 2H), 7.29–7.39 (m, 2H), 7.11 (t, 1H), 7.00 (d, 2H), 4.87 (t, 1H), 4.71 (t, 1H), 4.31 (t, 1H), 4.22 (s, 3H), 4.03 (s, 3H), 2.31 (s, 3H); EI/MS 445 m/e (M+1).

Example 7

3-(2-Chloro-6-fluorophenyl)-5-{5-[4-(1.1,2,3,3,3-hexafluoropropoxy)phenyl]-4-methylthien-3-yl}-1-methyl-1H-1,2,4-triazole

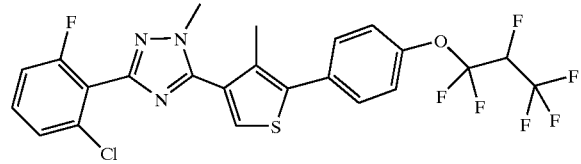

A solution of 3-(2-chloro-6-fluorophenyl)-5-[5-(4-hydroxyphenyl)-4-methylthien-3-yl]-1-methyl-1H-1,2,4-triazole (300 mg, 0.7 mmol) in dry DMF (3 mL) was treated with aqueous sodium hydroxide (25% solution, 120 mL, 3.5 mmol) at a dropwise rate. After stirring at room temperature for 30 minutes, hexafluoropropene was bubbled in for 35 minutes and then stirred at room temperature for 40 minutes. The reactants were poured into water (50 mL) and extracted with ether (3×40 mL). The combined ethereal extracts were washed with water (4×150 mL) until the aqueous washings were neutral and then with brine (100 mL), dried over magnesium sulphate, and concentrated. Column chromatography afforded a colourless gum (0.24 g, 58%): $^1$H NMR (CDCl$_3$) δ 7.55 (s, 1H), 7.49 (d, 2H), 7.26–7.39 (m, 4H), 7.11 (t, 1H), 5.10 & 4.95 (d sextets, 1H), 4.03 (s, 3H), 2.33 (s, 3H); EI/MS 549 (M+1).

The following compounds were prepared according to the general procedure of Example 7.

3-(2-Chloro-6-fluorophenyl)-5-{5-[4-(2,2-dichloro-1,1-difluoroethoxy)phenyl]-4-methylthien-3-yl}-1-methyl-1H-1,2,4-triazole

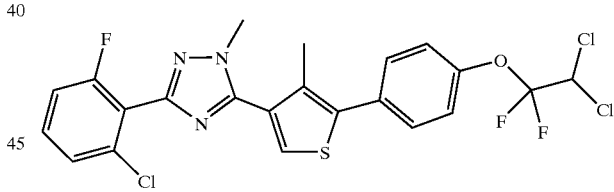

The product was isolated as a pale, yellow foam (58% yield): $^1$H NMR (CDCl$_3$) δ 7.54 (s, 1H), 7.48 (d, 2H), 7.29–7.39 (m, 4H), 7.11 (t, 1H), 5.95 (t, 1H), 4.03 (s, 3H), 2.33 (s, 3H); EI/MS 533 m/e (M$^+$).

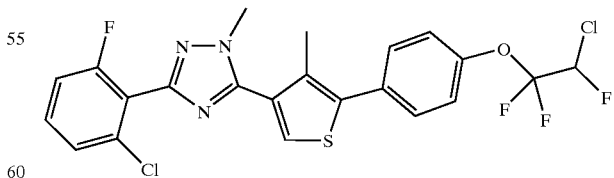

3-(2-Chloro-6-fluorophenyl)-5-{5-[4-(2-chloro-1,1,2-trifluoroethoxy)phenyl]-4-methylthien-3-yl}-1-methyl-1H-1,2,4-triazole The product was isolated as a colourless glass (78% yield): $^1$H NMR (CDCl$_3$) δ 7.55 (s, 1H), 7.49 (d, 2H), 7.29–7.39 (m, 4H), 7.11 (t, 1H), 6.38 & 6.22 (t, 1H), 4.03 (s, 3H), 2.33 (s, 3H); EI/MS 515 m/e (M−1); Calcd. for C$_{22}$H$_{15}$Cl$_2$F$_4$N$_3$O$_2$S: C, 51.3; H, 2.94; N, 8.16; S, 6.21; Found: C, 51.2; H, 3.01; N, 8.07; S, 6.21.

3-(2-Chloro-6-fluorophenyl)-5-{5-[4-(2-bromo-1,1,2-trifluoroethoxy)phenyl]-4-methylthien-3-yl}-1-methyl-1H-1,2,4-triazole

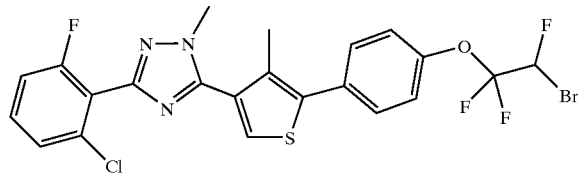

The product was isolated as a white solid (76% yield): mp 80–82° C.; $^1$H NMR (CDCl$_3$) δ 7.55 (s, 1H), 7.49 (d, 2H), 7.29–7.39 (m, 4H), 7.11 (t, 1H), 6.64 & 6.48 (t, 1H), 4.03 (s, 3H), 2.33 (s, 3H); EI/MS 562 m/e (M+1).

3-(2-Chloro-6-fluorophenyl)-5-[5-(4-difluoromethoxyphenyl)-4-methylthien-3-yl]-1-methyl-1H-1,2,4-triazole

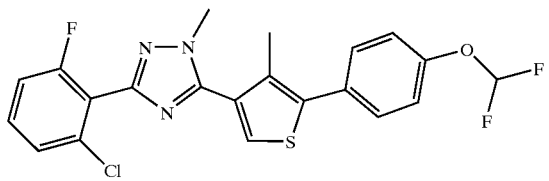

The product was isolated as an amorphous white solid (52% yield): mp 115–116° C.; $^1$H NMR (CDCl$_3$) δ 7.53 (s, 1H), 7.47 (d, 2H), 7.29–7.45 (m, 2H), 7.20 (d, 2H), 7.11 (t, 1H), 6.57 (t, J=73.8 Hz, 1H), 4.03 (s, 3H), 2.32 (s, 3H); EI/MS 450 (M$^+$).

3-(2-Chloro-6-fluorophenyl)-5-{5-[4-(2-chloro-1,1,2-trifluoroethoxy)phenyl]-3-methylthien-2-yl}-1-methyl-1H-1,2,4-triazole

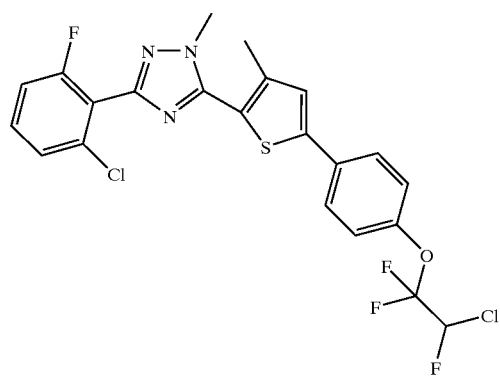

The product was isolated as a white solid (65% yield): mp 115–116° C.; $^1$H NMR (CDCl$_3$) δ 7.55 (d, 2H), 7.11–7.31 (m, 5H), 7.02 (t, 1H), 6.13 & 6.30 (t, 1H), 3.99 (s, 3H), 2.34 (s, 3H); EI/MS 515 m/e (M−1).

3-(2-Chloro-6-fluorophenyl)-5-{5-[4-(2,2-dichloro-1,1-difluoroethoxy)phenyl]-3-methylthien-2-yl}-1-methyl-1H-1,2,4-triazole

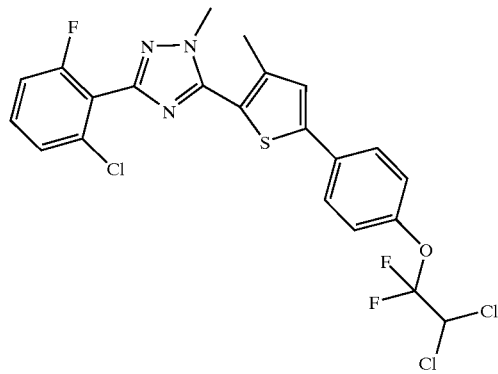

Product was isolated as a white solid (72% yield): mp 119–120° C.; $^1$H NMR (CDCl$_3$) δ 7.55 (d, 2H), 7.21–7.31 (m, 3H), 7.15 (s, 1H), 7.02 (t, 1H), 5.85 (t, 1H), 3.99 (s, 3H), 2.34 (s, 3H); EI/MS 534 m/e (M+1).

3-(2-Chloro-6-fluorophenyl)-5-{5-[4-(1,1,2,3,3,3-hexafluoropropoxy)phenyl]-3-methylthien-2-yl}-1-methyl-1H-1,2,4-triazole

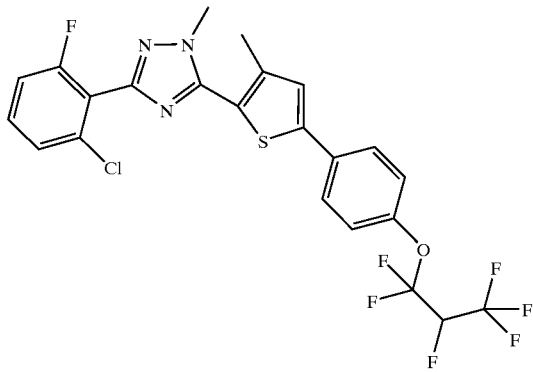

Product was isolated as a clear thick oil (58% yield): $^1$H NMR (CDCl$_3$) δ 7.48 (d, 2H), 7.15–7.22 (m, 3H), 7.11 (s, 1H), 6.99 (t, 1H), 4.79–4.95 (m, 1H), 3.93 (s, 3H), 2.27 (s, 3H); EI/MS 550 m/e (M+1).

3-(2-Chloro-6-fluorophenyl)-5-{5-[4-(2-bromo-1,1,2-trifluoroethoxy)phenyl]-3-chlorothien-2-yl}-1-methyl-1H-1,2,4-triazole

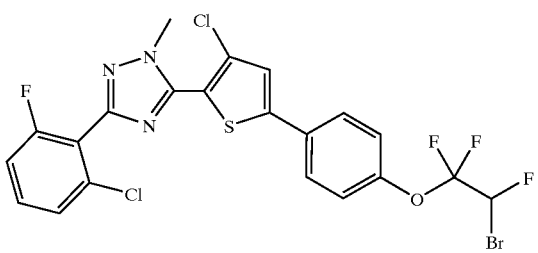

Product was isolated as a white crystalline solid (68% yield): mp 137–140° C.; $^1$H NMR (CDCl$_3$) δ 7.60 (m, 2H), 7.40–7.25 (m, 5H), 7.14–7.08 (m, 1H), 6.56 (dt, 1H, J$_{H,F\,(gem)}$=47.6 Hz, J$_{H,F(vic)}$=4.67 Hz,), 4.08 (s, 3H); EI/MS 581 m/e (M+); Calcd for C$_{21}$H$_{12}$BrCl$_2$F$_4$N$_3$OS: C, 43.40; H, 2.08; N, 7.23; Found: C, 43.51; H, 2.10; N, 7.11.

3-(2-Chloro-6-fluorophenyl)-5-{4-chloro-5-[4-(2-chloro-1,1,2-trifluoroethoxy)-phenyl]thien-3-yl}-1-methyl-1H-1,2,4-triazole

Product was isolated as a tan solid (71% yield): mp 82–87° C.; $^1$H NMR (CDCl$_3$) δ 7.71 (m, 3H), 7.40–7.30 (m, 4H), 7.15–7.09 (m, 1H), 6.30 (dt, 1H, J$_{H,F(gem)}$=47.9 Hz, J$_{H,F(vic)}$4.02 Hz), 4.01 (s, 3H); EI/MS 536 m/e (M+H); Calcd for C$_{21}$H$_{12}$Cl$_3$F$_4$N$_3$OS: C, 46.99; H, 2.25; N, 7.83; Found: C, 47.06; H, 2.45; N, 7.70.

3-(2-Chloro-6-fluorophenyl)-5-{5-[4-(2-chloro-1,1,2-trifluoroethoxy)phenyl]-3-chlorothien-2-yl}-1-methyl-1H-1,2,4-triazole

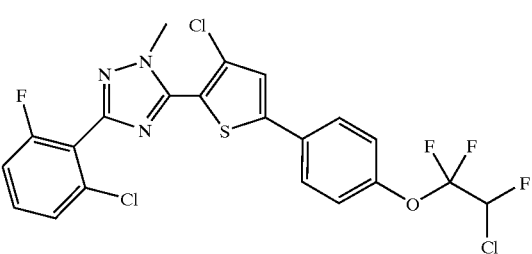

Product was isolated as a white solid (72% yield): mp 135–138° C.; $^1$H NMR (CDCl$_3$) δ 7.60 (m, 2H), 7.40–7.28 (m, 5H), 7.14–7.08 (m, 1H), 6.29 (dt, 1H, J$_{H,F(gem)}$=47.9 Hz, J$_{H,F(vic)}$3.93 Hz), 4.08 (s, 3H); EI/MS 535 m/e (M+); Calcd for C$_{21}$H$_{12}$Cl$_3$F$_4$N$_3$OS: C, 46.99; H, 2.25; N, 7.83; Found: C, 46.99; H, 2.31; N, 7.69.

3-(2-Chloro-6-fluorophenyl)-5-{4-[4-(2-bromo-1,1,2-trifluoroethoxy)phenyl]-3-methylthien-2-yl}-1-methyl-1H-1,2,4-triazole

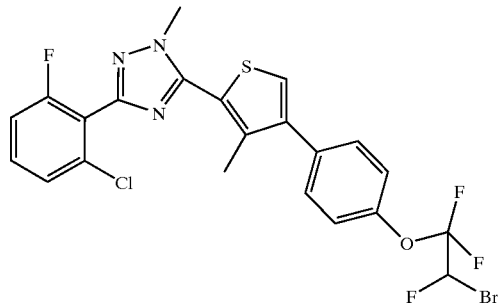

Product was isolated as a clear foam (70% yield): $^1$H NMR (CDCl$_3$) δ 2.32 (s, 3H), 4.07 (s, 3H), 6.57 (dt, 1H, J=47.9, 4.9, 4.4 Hz), 7.08–7.14 (m, 1H), 7.28–7.37 (m, 4H), 7.41 (d, 3H, J=7.3 Hz); EI/MS 560 m/e (M+H); Calcd. for C$_{22}$H$_{15}$ClBrF$_4$N$_3$OS: C, 47.12; H, 2.70; N, 7.49; Found: C, 47.35; H, 2.78; N, 7.36.

3-(2-Chloro-6-fluorophenyl)-5-{4-[4-(2-chloro-1,1,2-trifluoroethoxy)phenyl]-3-methylthien-2-yl}-1-methyl-1H-1,2,4-triazole

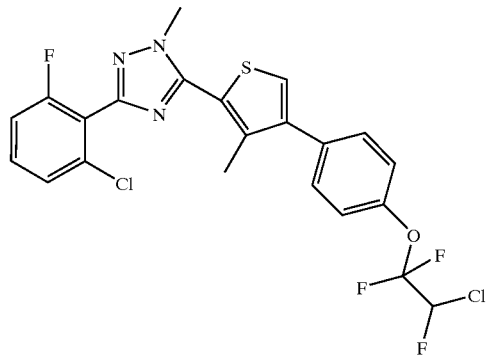

Product was isolated as a clear oil (71% yield): $^1$H NMR (CDCl$_3$) δ 2.32 (s, 3H), 4.07 (s, 3H), 6.30 (dt, 1H, J=48.1, 4.1 Hz), 7.08–7.14 (m, 1H), 7.27–7.43 (m, 7H); EI/MS 516 m/e (M+H).

3-(2-Chloro-6-fluorophenyl)-5-{4-[4-(1,1,2,3,3,3-hexafluoropropoxy)phenyl]-3-methylthien-2-yl}-1-methyl-1H-1,2,4-triazole

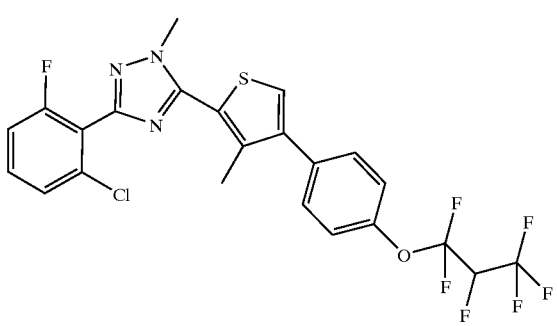

Product was isolated as a clear oil (44% yield): $^1$H NMR (CDCl$_3$) δ 2.32 (s, 3H), 4.06 (s, 3H), 5.03 (m, 1H), 7.08–7.14 (m, 1H), 7.29–7.37 (m, 4H), 7.39–7.44 (m, 3H); EI/MS 549 m/e (M+H); Calcd. for C$_{23}$H$_{15}$ClF$_7$N$_3$OS: C, 50.24; H, 2.75; N, 7.64; Found: C, 50.36; H, 3.01; N, 7.39.

3-(2-Chloro-6-fluorophenyl)-5-(4-{4-[(2,2-dichloro-1-fluorovinyl)oxy]phenyl}-3-methylthien-2-yl)-1-methyl-1H-1,2,4-triazole

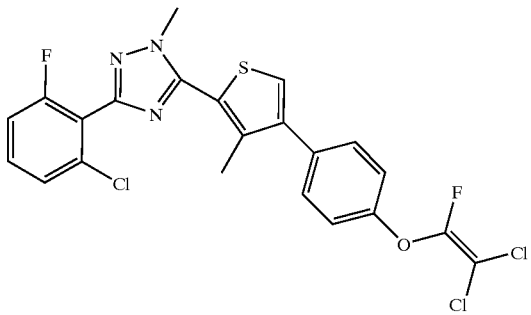

Product was isolated as a clear oil (10% yield): ¹H NMR (CDCl₃) δ 2.31 (s, 3H), 4.06 (s, 3H), 7.08–7.17 (m, 3H), 7.29–7.37 (m, 2H), 7.38–7.42 (m, 3H); EI/MS 512 m/e (M+H).

3-(2-Chloro-6-fluorophenyl)-5-{4-[4-(2,2-dichloro-1,1-difluoroethoxy)phenyl]-3-methylthien-2-yl}-1-methyl-1H-1,2,4-triazole

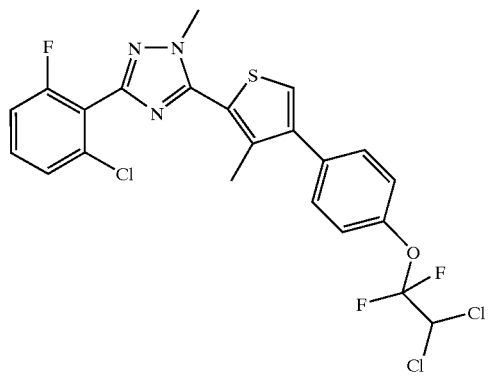

Product was isolated as a white waxy solid (53% yield): mp 114–116° C.; ¹H NMR (CDCl₃) δ 2.32 (s, 3H), 4.07 (s, 3H), 5.95 (t, 1H, J=4.8, 4.4 Hz), 7.08–7.14 (m, 1H), 7.28–7.38 (m, 4H), 7.39–7.42 (m, 3H); EI/MS 532 m/e (M+H).

Example 8

3-(2-Chloro-6-fluorophenyl)-5-[3-methyl-4-bromo-5-(4-trifluoromethoxyphenyl)-2-thienyl]-1-ethyl-[1,2,4]-triazole

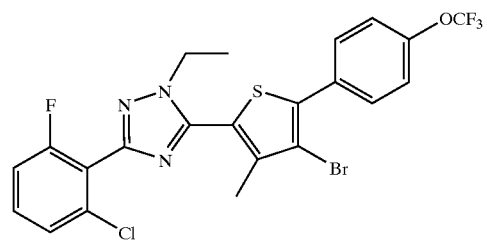

Methyl-N-{[3-methyl-4-bromo-5-(4-trifluoromethoxyphenyl)-2-thienyl]-carbonyl}-2-fluoro-6-chlorobenzenecarbimidothioate (0.85 g, 1.5 mmol) and ethylhydrazine oxalate (0.90 g, 6 mmol) were combined in toluene (5 mL) and stirred 64 h at 25° C. and heated to reflux for 18 h. The reaction mixture was diluted with ether and washed with 0.1 M hydrochloric acid and brine, dried over anhydrous magnesium sulfate and concentrated to a crude pale yellow oil. Chromatography (silica gel, 10% ethylacetate/hexane) afforded the product as a clear oil (0.250 mg, 30%): ¹H NMR (CDCl₃) δ 7.73 (2H, d), 7.0–7.5 (5H, m), 4.3 (2H, q), 2.40 (3H, s), 1.55 (3H, t); EI/MS 546 m/e (M⁺).

Example 9

5-{5-Bromo-4-[4-(2-bromo-1,1,2-trifluoroethoxy)phenyl]-3-methylthien-2-yl}-3-(2-chloro-6-fluorophenyl)-1-methyl-1H-1,2,4-triazole

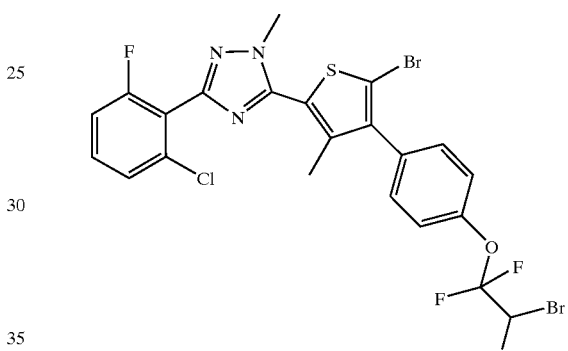

Bromine (0.03 g, 0.2 mmol) in acetic acid (0.5 mL) was added dropwise to a solution of 5-{4-[4-(2-bromo-1,1,2-trifluoroethoxy)phenyl]-3-methylthien-2-yl}-3-(2-chloro-6-fluorophenyl)-1-methyl-1H-1,2,4-triazole (0.1 g, 0.2 mmol) in acetic acid (1 mL) at 0° C. The reaction was allowed to warm to 25° C. and stirred for 50 h. The reaction mixture was made basic with saturated aq NaHCO₃ (30 mL) and extracted with ether (3×30 mL). The combined ether extracts were washed with brine, dried over sodium sulfate, filtered, and the solvent removed under reduced pressure to give crude product. Column chromatography gave the product as a clear oil (88 mg, 77%): ¹H NMR (CDCl₃) δ 2.19 (s, 3H), 4.06 (s, 3H), 6.58 (dt, 1H, J=47.6, 5.1, 4.0, 4.4 Hz), 7.08–7.14 (m, 1H), 7.29–7.40 (m, 6H), EI/MS 636 m/e (M+H).

Example 10

The compounds identified in the following Tables 1–4 were prepared using the procedures illustrated in the foregoing examples, and the compounds were tested against tobacco budworm, beet armyworm, cabbage looper, cotton aphid, two-spotted spider mite, and sweetpotato whitefly using procedures described hereinafter.

TABLE 1
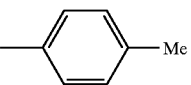
| R¹ | R² | Y | Ar | TBW | BAW | CL | CA | SM | WF |
|---|---|---|---|---|---|---|---|---|---|
| Cl | Cl | Cl | 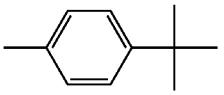 | G | A | E | C | G | C |
| Cl | Cl | Cl | 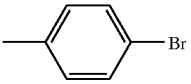 | B | D | F | E | G | F |
| Cl | Cl | Cl | 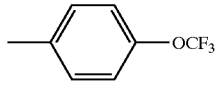 | G | A | A | C | G | E |
| Cl | Cl | Cl | 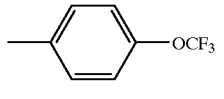 | G | G | D | C | A | C |
| CH₃ | H | Cl | 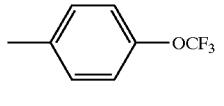 | D | A | B | A | A | G |
| CH₃ | Br | Cl | 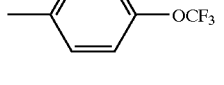 | G | A | G | A | A | G |
| Cl | H | F | 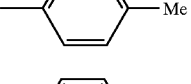 | B | A | B | F | F | G |
| Cl | H | F | 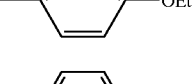 | G | A | B | G | G | G |
| Cl | H | F | 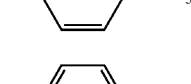 | G | B | A | D | F | G |
| CH₃ | H | F | 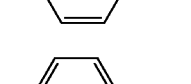 | F | A | A | A | A | F |
| Cl | H | F | 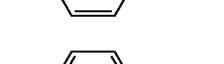 | G | A | A | G | F | G |
| H | Br | Cl | 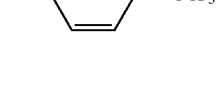 | G | A | A | G | A | F |
| Cl | H | Cl | 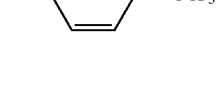 | A | A | A | C | A | G |

TABLE 1-continued
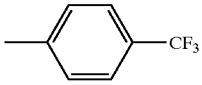
| R¹ | R² | Y | Ar | TBW | BAW | CL | CA | SM | WF |
|---|---|---|---|---|---|---|---|---|---|
| Cl | H | Cl | 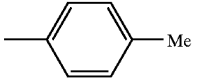 —⟨ ⟩—CF₃ | A | A | A | D | A | F |
| Cl | H | Cl | —⟨ ⟩—Me | G | A | D | F | G | G |
| Cl | H | Cl | —⟨ ⟩—OEt | G | A | D | B | A | G |
| Cl | Br | Cl | —⟨ ⟩—OCF₃ | D | B | A | A | C | F |
| Cl | H | Cl | —⟨ ⟩—Br | A | A | A | B | A | G |
| CH₃ | H | Cl | —⟨ ⟩—OEt | G | A | D | B | G | F |
| CH₃ | H | Cl | —⟨ ⟩—Cl | D | A | A | A | A | D |
| Cl | Br | Cl | —⟨ ⟩—CF₃ | F | A | A | A | G | G |
| Cl | Br | Cl | —⟨ ⟩—OEt | F | D | A | A | F | G |
| CH₃ | H | Cl | 3-Cl, 4-F phenyl | G | D | A | B | A | G |
| CH₃ | H | Cl | 3-OCF₃ phenyl | G | G | A | B | A | F |
| CH₃ | H | Cl | —⟨ ⟩—F | F | D | A | B | A | G |

TABLE 1-continued
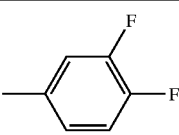
| R¹ | R² | Y | Ar | TBW | BAW | CL | CA | SM | WF |
|---|---|---|---|---|---|---|---|---|---|
| CH₃ | H | Cl | 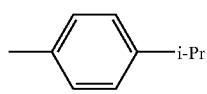 | F | D | A | A | A | A |
| CH₃ | H | Cl | 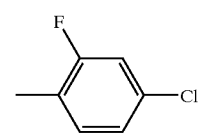 | F | A | A | C | A | G |
| CH₃ | H | Cl | 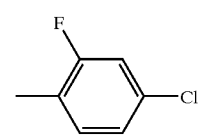 | B | A | A | A | A | G |
| CH₃ | H | Cl | 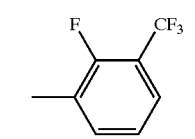 | F | A | A | C | A | G |
| CH₃ | H | Cl | 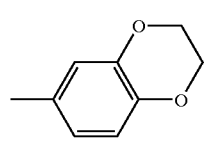 | D | A | A | D | A | G |
| CH₃ | H | Cl | 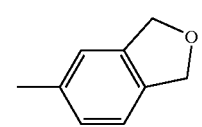 | G | A | A | B | B | G |
| CH₃ | H | Cl | 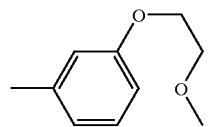 | G | B | A | D | C | G |
| CH₃ | H | Cl | 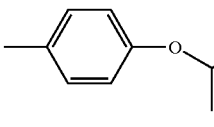 | F | F | G | B | C | G |
| CH₃ | H | Cl | 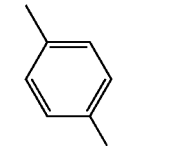 | G | D | B | D | A |  |
| CH₃ | H | Cl | 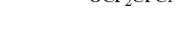 | A | A | A | D | A | F |

TABLE 1-continued
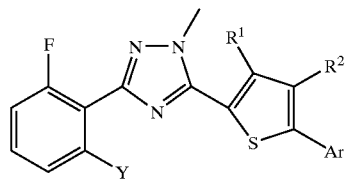
| R¹ | R² | Y | Ar | TBW | BAW | CL | CA | SM | WF |
|---|---|---|---|---|---|---|---|---|---|
| CH₃ | H | Cl | | A | A | A | A | B | E |
| CH₃ | H | Cl | | A | A | A | B | A | F |
| Cl | H | Cl | | A | A | A | E | C | G |
TABLE 2
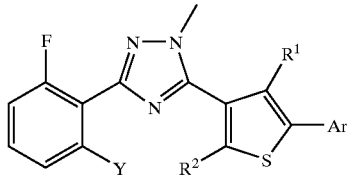
| R¹ | R² | Y | Ar | TBW | BAW | CL | CA | SM | WF |
|---|---|---|---|---|---|---|---|---|---|
| CH₃ | H | Cl | | D | A | A | A | A | A |
| CH₃ | H | Cl | | G | D | G | A | B | G |
| CH₃ | H | Cl | | G | B | F | A | A | F |
| CH₃ | H | Cl | | G | B | A | B | G | A |
| CH₃ | H | Cl | | G | D | G | B | E | G |

TABLE 2-continued
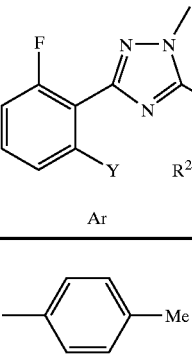
| R¹ | R² | Y | Ar | TBW | BAW | CL | CA | SM | WF |
|---|---|---|---|---|---|---|---|---|---|
| CH₃ | H | Cl | 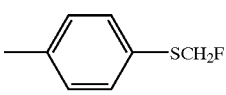 —Me | G | D | A | A | G | G |
| CH₃ | H | Cl | 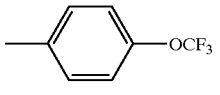 —SCH₂F | G | B | G | B |  | F |
| CH₃ | Br | Cl | 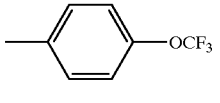 —OCF₃ | G | A | A | B | F | D |
| CH₃ | CH₃ | Cl | 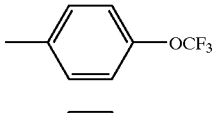 —OCF₃ | G | A | A | A | A | E |
| CH₃ | Cl | Cl | 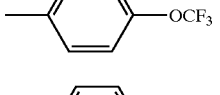 —OCF₃ | B | A | A | C | F | G |
| H | H | Cl | 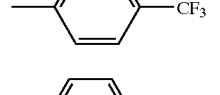 —OCF₃ | F | A | A | D | G | G |
| H | H | Cl |  —CF₃ | A | A | A | F | G | G |
| H | H | F | 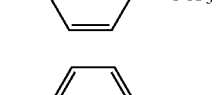 —OCF₃ | D | G | A | A | G | G |
| H | Br | Cl | 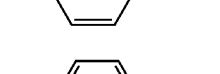 —OCF₃ | B | A | A | B | A | G |
| CH₃ | H | Cl | 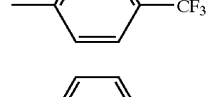 —OMe | G | G | B | A | G | B |
| H | H | F | 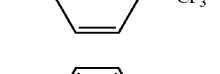 —CF₃ | G | G | A | C | G | G |
| H | Br | Cl | 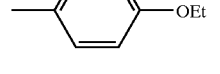 —CF₃ | A | A | A | G | G | G |
| H | H | Cl |  —OEt | G | F | A | A | A | G |

TABLE 2-continued

| R¹ | R² | Y | Ar | TBW | BAW | CL | CA | SM | WF |
|---|---|---|---|---|---|---|---|---|---|
| H | CH₃ | Cl | 4-(OCF₃)C₆H₄ | A | A | A | A | A | G |
| CH₃ | H | Cl | 3-(OCF₃)C₆H₄ | G | G | A | A | F | B |
| CH₃ | H | Cl | 4-(OPh)C₆H₄ | F | A | A | A | A | A |
| CH₃ | H | Cl | 4-(O-nPr)C₆H₄ | G | A | A | A | G | A |
| CH₃ | H | Cl | 4-(OCH₂CF₃)C₆H₄ | A | A | A | B | A | A |
| CH₃ | H | Cl | 3-(CF₃)C₆H₄ | G | G | A | A | B | A |
| CH₃ | H | Cl | 4-(OCF₂CFCF₃)C₆H₄ | A | A | A | D | B | A |
| CH₃ | H | Cl | 4-(OCF₂CFCl)C₆H₄ | A | A | A | B | A | A |

TABLE 2-continued
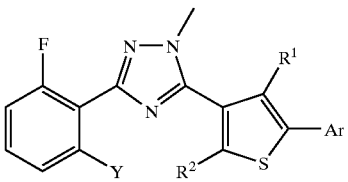
| R¹ | R² | Y | Ar | TBW | BAW | CL | CA | SM | WF |
|---|---|---|---|---|---|---|---|---|---|
| CH₃ | H | Cl | 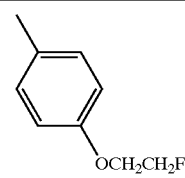 | G | A | F | A | G | A |
| CH₃ | H | Cl | 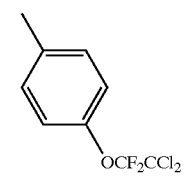 | A | A | A | B | A | A |
| CH₃ | H | Cl | 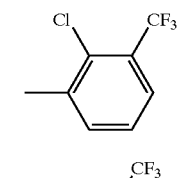 | G | G | A | B | A | G |
| CH₃ | H | Cl | 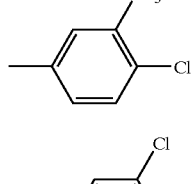 | B | A | A | A | A | G |
| CH₃ | H | Cl | 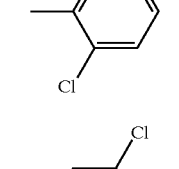 | G | G | D | C | G | F |
| CH₃ | H | Cl | 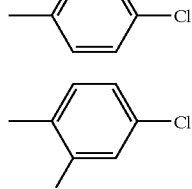 | F | D | A | A | F | F |
| CH₃ | H | Cl | 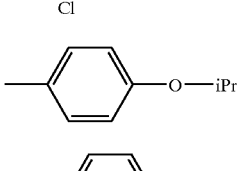 | D | G | A | A | G | G |
| CH₃ | H | Cl | 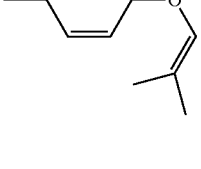 | F | G | G | A | G | G |
| CH₃ | H | Cl |  | F | A | A | A | A | A |

TABLE 2-continued
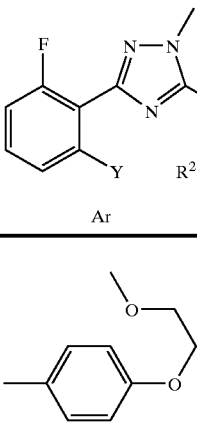
| R¹ | R² | Y | Ar | TBW | BAW | CL | CA | SM | WF |
|---|---|---|---|---|---|---|---|---|---|
| CH₃ | H | Cl | 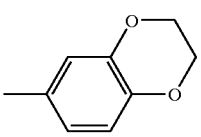 | G | B | B | C | D | F |
| CH₃ | H | Cl | 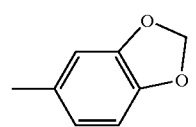 | G | D | A | B | G | G |
| CH₃ | H | Cl | 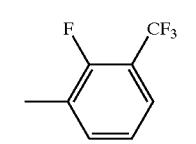 | F | G | A | B | F | F |
| CH₃ | H | Cl | 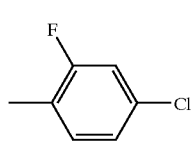 | G | G | A | A | F | E |
| CH₃ | H | Cl | 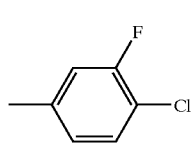 | F | G | A | A | A | G |
| CH₃ | H | Cl | 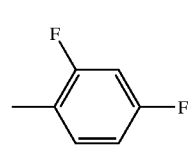 | G | F | A | A | A | G |
| CH₃ | H | Cl | 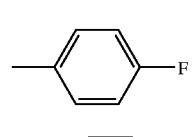 | G | G | A | B | B | F |
| CH₃ | H | Cl | 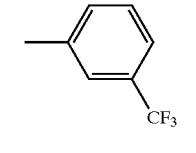 | F | G | D | B | B | F |
| H | H | Cl | 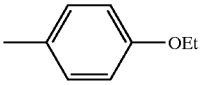 | F | G | B | G | G | |
| H | Cl | Cl | | G | A | A | A | A | G |

TABLE 2-continued

| R¹ | R² | Y | Ar | TBW | BAW | CL | CA | SM | WF |
|---|---|---|---|---|---|---|---|---|---|
| H | Cl | Cl | 4-CF₃-phenyl | A | A | A | F | A | G |
| H | H | Cl | 3-F-4-CF₃-phenyl | D | A | A | C | C | F |
| H | Cl | Cl | 2,3-dihydrobenzofuran-6-yl | F | G | A | C | G | G |
| H | Cl | Cl | 3-OCF₃-phenyl | G | G | A | A | A | G |
| H | Cl | Cl | 3-CF₃-phenyl | G | G | B | A |  | G |
| H | H | Cl | 2-F-4-Cl-phenyl | F | G | A | B | A | F |
| H | Cl | Cl | 3-F-4-CF₃-phenyl | F | A | A | F | G | F |
| H | CH₃ | Cl | 4-CF₃-phenyl | A | A | A | F | A | G |
| H | CH₃ | Cl | 4-OEt-phenyl | G | A | D | B | A | C |
| H | Cl | Cl | 3-F-4-CF₃-phenyl | F | A | A | F | A | F |

TABLE 2-continued

| R¹ | R² | Y | Ar | TBW | BAW | CL | CA | SM | WF |
|---|---|---|---|---|---|---|---|---|---|
| H | Cl | Cl | 4-(OCF₃)phenyl | F | A | A | F | A | |
| H | CH₃ | Cl | 3-fluoro-4-methyl-(4-Me)phenyl (3-F, 4-Me with Me at para) | G | D | G | C | A | F |
| H | CH₃ | Cl | 3-(OCF₃)phenyl | G | G | A | A | A | F |
| H | CH₃ | Cl | 3-fluoro-4-(CF₃)phenyl | G | A | B | A | | F |
| H | CH₃ | Cl | 3,4-dichlorophenyl | F | A | A | F | A | G |
| H | CH₃ | Cl | 3-fluorophenyl | G | F | A | B | G | G |
| CH₃ | H | Cl | 3-fluoro-4-(CF₃)phenyl | B | A | A | A | F | A |
| CH₃ | CH₃ | Cl | 4-(CF₃)phenyl | D | A | A | B | F | G |
| CH₃ | CH₃ | Cl | 3-fluoro-4-(CF₃)phenyl | G | A | A | B | | |
| H | CH₃ | Cl | 3-fluoro-4-(CF₃)phenyl | G | A | A | F | B | G |

TABLE 2-continued

| R¹ | R² | Y | Ar | TBW | BAW | CL | CA | SM | WF |
|---|---|---|---|---|---|---|---|---|---|
| H | H | Cl | 4-Me-3-F-phenyl (Me, F substituents) | G | G | F | C | F | G |
| CH₃ | H | Cl | 4-CF₃-2-F-phenyl | G | G | A | B | F | F |
| H | CH₃ | Cl | 4-CF₃-2-F-phenyl | F | G | G | D | G | G |
| CH₃ | CH₃ | Cl | 4-OEt-phenyl | G | A | A | A | C | F |
| CH₃ | H | Cl | 4-OCF₂CFBr-phenyl | A | A | A | A | A | A |
| Cl | H | Cl | 4-OCF₃-phenyl | B | B | A | B | C | A |
| Cl | H | Cl | 4-CF₃-phenyl | A | B | A | C | C | E |
| CH₃ | H | Cl | 4-iPr-phenyl | G | B | A | C | E | A |
| CH₃ | H | F | 4-CF₃-3-Cl-phenyl | G | G | A | E | G | G |
| Cl | H | Cl | 4-OEt-phenyl | F | A | A | B | A | A |

TABLE 2-continued

| R¹ | R² | Y | Ar | TBW | BAW | CL | CA | SM | WF |
|---|---|---|---|---|---|---|---|---|---|
| CH₃ | H | Cl | 2-methyl-3-fluoro-5-trifluoromethylphenyl | A | A | A | B | F | A |
| CH₃ | H | Cl | 4-(difluoromethoxy)-2-methylphenyl | A | A | A | C | B | A |
| CH₃ | H | Cl | 4-(tetrahydropyran-2-yloxy)-2-methylphenyl | F | A | F | B | F | F |
| CH₃ | H | Cl | 4-(1,1,2,2-tetrafluoroethoxy)-2-methylphenyl | A | A | A | C | E | A |
| CH₃ | C₂H₅ | Cl | 4-(trifluoromethoxy)-2-methylphenyl | B | A | A | B | G | G |
| CH₃ | CH₃ | Cl | 4-(1,1,2,3,3,3-hexafluoropropoxy)-2-methylphenyl | A | A | A | E | G | G |
| CH₃ | C₂H₅ | Cl | 4-ethoxy-2-methylphenyl | F | A | A | B | G | F |

TABLE 3
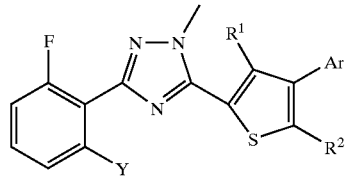
| R¹ | R² | Y | Ar | TBW | BAW | CL | CA | SM | WF |
|---|---|---|---|---|---|---|---|---|---|
| CH₃ | H | Cl | ―⟨⟩―OCF₃ | A | A | A | A | A | A |
| CH₃ | H | Cl | ―⟨⟩―CF₃ | D | D | G | D | A | F |
| CH₃ | Br | Cl | ―⟨⟩―OCF₃ | G | E | C | A | G | G |
| CH₃ | Cl | Cl | ―⟨⟩―OCF₃ | G | A | G | A | C | F |
| CH₃ | H | Cl | ―⟨⟩―OEt | E | A | A | B | A | A |
| CH₃ | H | Cl | ―⟨⟩―OCF₂CFBr | B | A | A | A | G | A |
| CH₃ | H | Cl | ―⟨⟩―OCF₂CFCl | B | A | A | B | C | A |
| CH₃ | H | Cl | ―⟨⟩―OCF₂CFCF₃ | A | A | A | D | A | A |
| CH₃ | Br | Cl | ―⟨⟩―OCF₂CFBr | F | A | A | B | G | F |

TABLE 4

| R¹ | R² | R³ | Y | Ar | TBW | BAW | CL | CA | SM | WF |
|---|---|---|---|---|---|---|---|---|---|---|
| CH₃ | Br | Et | Cl | ⟨C₆H₄⟩—OCF₃ | G | A | A | C | C | F |

TBW refers to activity at 400 ppm against tobacco budworm,
BAW refers to activity at 400 ppm against beet armyworm,
CL refers to activity at 400 ppm against cabbage looper,
CA refers to activity at 50 ppm against cotton aphid,
SM refers to activity at 2.5 ppm against two-spotted spider mite,
WF refers to activity at 200 ppm against whitefly.

In each case the rating scale is as follows

| % Control | Rating |
|---|---|
| 90–100 | A |
| 80–89 | B |
| 70–79 | C |
| 60–69 | D |
| 50–59 | E |
| less than 50 | F |
| Inactive | G |

Insecticide and Miticide Utility

The compounds of the invention are useful for the control of insects and mites. Therefore, the present invention also is directed to a method for inhibiting an insect or mite which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, insects or mites which eat or contact edible or ornamental plants can be controlled by applying the active compound to plant parts such as the seed, seedling, or cutting which is planted, the leaves, stems, fruits, grain, or roots, or to the soil in which the roots are growing. It is contemplated that the compounds might also be useful to protect textiles, paper, stored grain, seeds, domesticated animals, buildings or human beings by applying an active compound to or near such objects. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm by weight active compound is used. For example, insects and mites which can be inhibited include, but are not limited to:

Lepidoptera—*Heliothis* spp., *Helicoverpa* spp., *Spodoptera* spp., *Mythimna unipuncta, Agrotis ipsilon, Earias* spp., *Euxoa auxiliaris, Trichoplusia ni, Anticarsia gemmatalis, Rachiplusia nu, Plutella xylostella, Chilo* spp., *Scirpophaga incertulas, Sesamia inferens, Cnaphalocrocis medinalis, Ostrinia nubilalis, Cydia pomonella, Carposina niponensis, Adoxophyes orana, Archips argyrospilus, Pandemis heparana, Epinotia aporema, Eupoecilia ambiguella, Lobesia botrana, Polychrosis viteana, Pectinophora gossypiella, Pieris rapae, Phyllonorycter* spp., *Leucoptera malifoliella, Phyllocnisitis citrella*

Coleoptera—*Diabrotica* spp., *Leptinotarsa decemlineata, Oulema oryzae, Anthonomus grandis, Lissorhoptrus oryzophilus, Agriotes* spp., *Melanotus communis, Popillia japonica, Cyclocephala* spp., *Tribolium* spp.

Homoptera—*Aphis* spp., *Myzus persicae, Rhopalosiphum* spp., *Dysaphis plantaginea, Toxoptera* spp., *Macrosiphum euphorbiae, Aulacorthum solani, Sitobion avenae, Metopolophium dirhodum, Schizaphis graminum, Brachycolus noxius, Nephotettix* spp., *Nilaparvata lugens, Sogatella furcifera, Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*

Hemiptera—*Lygus* spp., *Eurygaster maura, Nezara viridula, Piezodorus guildingi, Leptocorisa varicornis*

Thysanoptera—*Frankliniella occidentalis, Thrips* spp., *Scirtothrips dorsalis*

Isoptera—*Reticulitermes flavipes, Coptotermes formosanus*

Orthoptera—*Blattella germanica, Blatta orientalis, Gryllotalpa* spp.

Diptera—*Liriomyza* spp., *Musca domestica, Aedes* spp., *Culex* spp., *Anopheles* spp.

Hymenoptera—*Iridomyrmex humilis, Solenopsis* spp., *Monomorium pharaonis, Atta* spp., *Pogonomyrmex* spp., *Camponotus* spp.

Siphonaptera—*Ctenophalides* spp., *Pulex irritans*

Acarina—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.

Insecticidal test for Tobacco Budworm (*Heliothis virescens*), Beet Armyworm (*Spodoptera exigua*), and Cabbage Looper (*Trichoplusia ni*).

To prepare test solution, the test compound was formulated at 400 ppm in 7.5 mL of 2 acetone: 1 tap water. 250 mL of the test solution was pipetted upon the surface of 8 mL of lepidopteran diet (modified Shorey) contained in each of five one-ounce plastic cups (one cup=1 replication). A second-instar beet armyworm was placed upon the treated diet in each cup once the solvent had air-dried. The solutions remaining after completing applications to the one-ounce cups were then used as leaf-dip solutions for 3.5 cm leaf discs cut from cabbage leaves and cotton cotyledons. Five discs of each type of plant were dipped until thoroughly coated into each rate of each compound (=5 replications of each treatment). After air-drying, the treated leaf discs were placed individually into one-ounce plastic cups. Each dried, treated cotton cotyledon disc was infested with a $2^{nd}$ instar tobacco budworm larva, and each cabbage leaf disc was infested with a $2^{nd}$ instar cabbage looper larva. Cups containing the treated substrates and larvae were capped and then held in a growth chamber at 25° C., 50–55% RH, and 14 hr light: 10 hr dark for 5 days. The number of dead insects of 5 per species per treatment was then determined and the results are given in Tables 1–4.

Insecticidal Test for Cotton Aphid (*Aphis gossypii*)

To prepare spray solutions, 1 mg of each test compound was dissolved into 1 mL of a 90:10 acetone:ethanol solvent. This 1 mL of chemical solution was added to 19 mL of water containing 0.05% Tween 20 surfactant to produce a 50 ppm spray solution.

Squash cotyledons were infested with cotton aphid (all life stages)16–20 hours prior to application of spray solution. The solution was sprayed on both sides of each infested squash cotyledon (0.5 mL×2 each side) with a sweeping action until runoff. The plants were allowed to air dry and held for 3 days in a controlled room at 26° C. and 40% RH after which time the test was graded. Grading was by actual count using a dissecting microscope and comparison of test counts to the untreated check. Results are given in Tables 1–4 as percent control based on population reduction versus the untreated.

Insecticidal Test for Two-Spotted Spider Mite (*Tetranychus urticae*)

Ovicide Method:

Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24° C. and 90% RH for 6 days. Percent control based on the number of hatched larvae on treated discs and the number on untreated discs is reported in Tables 1–4.

Insecticidal test for Sweetpotato Whitefly (*Bemisia tabacia*)

Four mg of each test compound was dissolved by adding 4 mL of a 90:10 acetone:ethanol solvent mixture to the vial containing the sample compound. This solution was added to 16 mL of water containing 0.05% Tween 20 surfactant to produce 20 mL of an 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs (3rd–4th instar) per leaf.

Percent control based on reduction of large nymphs of a test compound compared to solution-only (no test compound) sprayed plants is reported in Tables 1–4.

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect and mite eggs to resist toxicant action, repeated applications may be desirable to control newly emerged larvae, as is true of other known insecticides and acaricides.

What is claimed is:

1. A compound of the formula wherein

X and Y independently represent Cl or F;

$R^1$ and $R^2$ independently represent H, $C_1$–$C_6$ alkyl or halogen;

$R^3$ represents $C_1$–$C_3$ alkyl;

$R^4$ represents $C_1$–$C_6$ haloalkyl, $C_1$–$C_6$ haloalkoxy or phenoxy;

$R^5$ represents H or halogen;

or a phytologically acceptable acid addition salt thereof.

2. A compound of claim 1 in which $R^3$ is $CH_3$.

3. A compound of claim 1 in which X is F and Y is Cl.

4. A compound of claim 1 in which $R^1$ is H or $CH_3$.

5. A compound of claim 1 in which $R^2$ is H or $CH_3$.

6. A compound of claim 1 in which $R^4$ is $CF_3$, haloalkoxy or phenoxy.

7. A compound of claim 1 in which $R^5$ is H, F or Cl.

8. A composition for controlling lepidoptera, coleoptera, mites and other sucking pests which comprises a compound of the formula wherein X and Y independently represent Cl or F;

$R^1$ and $R^2$ independently represent H, $C_1$–$C_6$ alkyl or halogen;

$R^3$ represent $C_1$–$C_3$ alkyl;

$R^4$ represents $C_1$–$C_6$ haloalkyl, $C_1$–$C_6$ haloalkoxy or phenoxy;

$R^5$ represents H or halogen;

or a phytologically acceptable acid addition salt thereof in combination with a phytologically-acceptable carrier.

9. A composition of claim 8 in which $R^3$ is $CH_3$.

10. A composition of claim 8 in which X is F andY is Cl.

11. A composition of claim 8 in which $R^1$ is H or $CH_3$.

12. A composition of claim 8 in which $R^2$ is or $CH_3$.

13. A composition of claim 8 in which $R^4$ is $CF_3$, haloalkoxy or phenoxy.

14. A composition of claim 8 in which $R^5$ is H, F or Cl.

15. A method of controlling lepidoptera, coleoptera, mites and other sucking pests which comprises applying to a locus where control is desired a lepidoptera-, coleoptera-, mite- or other sucking pest-inactivating amount of a compound of the formula

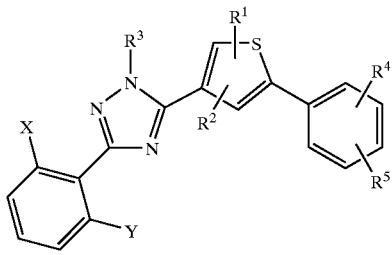

wherein
- X and Y independently represent Cl or F;
- $R^1$ and $R^2$ independently represent H, $C_1$–$C_6$ alkyl or halogen;
- $R^3$ represents $C_1$–$C_3$ alkyl;
- $R^4$ represents $C_1$–$C_6$ haloalkyl, $C_1$–$C_6$ haloalkoxy or phenoxy;
- $R^5$ represents H or halogen;

or a phytologically acceptable acid addition salt thereof in combination with a phytologically-acceptable carrier.

16. A method of claim 15 in which $R^3$ is $CH_3$.

17. A method of claim 15 in which X is F and Y is Cl.

18. A method of claim 15 in which $R^1$ is H or $CH_3$.

19. A method of claim 15 in which $R^2$ is H or $CH_3$.

20. A method of claim 15 in which $R^4$ is $CF_3$, haloalkoxy or phenoxy.

21. A method of claim 15 in which $R^5$ is H, F or Cl.

* * * * *